(12) United States Patent
Du et al.

(10) Patent No.: US 12,400,553 B2
(45) Date of Patent: Aug. 26, 2025

(54) SYSTEMS AND METHODS FOR REMOTE TRANSFERRING OF SENSATION TO GUIDE PHYSICAL MOTOR TRAINING

(71) Applicant: University of Florida Research Foundation, Incorporated, Gainesville, FL (US)

(72) Inventors: Jing Du, Gainesville, FL (US); Yang Ye, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 7 days.

(21) Appl. No.: 18/354,219

(22) Filed: Jul. 18, 2023

(65) Prior Publication Data

US 2024/0054906 A1     Feb. 15, 2024

Related U.S. Application Data

(60) Provisional application No. 63/371,016, filed on Aug. 10, 2022.

(51) Int. Cl.
| | |
|---|---|
| *G09B 5/02* | (2006.01) |
| *G06F 3/01* | (2006.01) |
| *G06T 13/40* | (2011.01) |
| *G06T 13/80* | (2011.01) |

(52) U.S. Cl.
CPC ............... *G09B 5/02* (2013.01); *G06F 3/011* (2013.01); *G06F 3/016* (2013.01); *G06T 13/40* (2013.01); *G06T 13/80* (2013.01)

(58) Field of Classification Search
CPC . G09B 5/02; G06F 3/011; G06F 3/016; G06T 13/40; G06T 13/80
See application file for complete search history.

(56) References Cited

U.S. PATENT DOCUMENTS

| | | | |
|---|---|---|---|
| 12,100,311 B1* | 9/2024 | Shattuck | G09B 19/003 |
| 2010/0286571 A1* | 11/2010 | Allum | A61B 5/486 |
| | | | 600/595 |
| 2015/0202492 A1* | 7/2015 | Domansky | A63F 13/00 |
| | | | 434/257 |

\* cited by examiner

*Primary Examiner* — Timothy A Musselman
(74) *Attorney, Agent, or Firm* — Alston & Bird LLP

(57) ABSTRACT

Systems and methods for remote human motor training. The method comprises generating visual guidance data based on first motion data received from a first client computing device, transmitting the visual guidance data to a second client computing device, receiving second motion data from the second client computing device, generating haptic guidance data based on a comparison of the second motion data with the first motion data, and transmitting the haptic guidance data to the second client computing device.

20 Claims, 18 Drawing Sheets

SYSTEMS AND METHODS FOR REMOTE TRANSFERRING OF SENSATION TO GUIDE PHYSICAL MOTOR TRAINING

CROSS REFERENCE TO RELATED APPLICATION

This application claims the priority of U.S. Provisional Application No. 63/371,016, entitled "SYSTEMS AND METHODS REMOTE TRANSFERRING OF SENSATION FOR PHYSICAL MOTOR TRAINING," filed on Aug. 10, 2022, the disclosure of which is hereby incorporated by reference in its entirety.

FIELD OF THE DISCLOSURE

The present application relates to virtual reality-based motor skill training, and in particular, a visual and haptic guidance system for conveying visual and haptic effects based on motions of one user to one or more other users.

BACKGROUND

Gym trainings (or body workout, strength trainings) involve a trainer and a trainee to be physically present in a same space. The trainer may show and guide the trainee to move different body components or muscle groups in the proper way. Although it is ideal to have the trainer and the trainee to present in the same space, conditions could happen that prevent them from meeting in person, such as social distancing or costs.

With the capability of providing immersive multimodalities experience, virtual reality ("VR") has been rapidly recognized and implemented for training. Motor training is one of the emerging topics for VR implementation. In motor training tasks, VR can provide multiple forms of supporting information including movement visualization, performance feedback, and contextual guidelines. VR-based motor skill training enables self-directed learning, with a virtual instructor and automated feedback, where trainees can practice motor skills as long and as many times as they wish without further costs, in a safe manner. In addition, game-like exercises or activities and immersive interaction in VR may promote enjoyment and motivation for training, which may enhance engagement in training and thus promote efficient human motor learning. VR-based human motor learning studies have also been pioneered in various domains, including rehabilitation, military, and industry, using game-like scenarios and different types of feedback modalities to promote human motor learning.

BRIEF SUMMARY

Various embodiments described herein relate to methods, apparatuses, systems, and non-transitory computer-readable storage media for remote human motor training.

According to one embodiment, the method comprises generating visual guidance data based on first motion data received from a first client computing device, transmitting the visual guidance data to a second client computing device, receiving second motion data from the second client computing device, generating haptic guidance data based on a comparison of the second motion data with the first motion data, and transmitting the haptic guidance data to the second client computing device.

In some embodiments, transmitting the haptic guidance data further comprises triggering hapto-tactile feedback. In some embodiments, the hapto-tactile feedback comprises vibration based at least in part on a degree of discrepancy between the first motion data and the second motion data. In some embodiments, the haptic guidance data comprises positive feedback representative of relatively accurate motion with respect to an exercise or activity based on the comparison of the second motion with the first motion data. In some embodiments, the haptic guidance data comprises feedback on one or more of body positioning, muscle activation, or movement pacing and control. In some embodiments, the first motion data comprises data representative of motion of a first user performing a set of body training tasks.

In some embodiments, the method further comprises formatting the first motion data into a filmbox format, registering one or more components to the formatted first motion data, and configuring animation of the one or more components by linking the formatted first motion data to motion of a virtual reality avatar. In some embodiments, registering the one or more components further comprises mapping motion tracking points based on the first motion data to the virtual reality avatar. In some embodiments, the method further comprises accessing animation files associated with the formatted first motion data and attaching the animation files to animation controllers configured to control motion of the virtual reality avatar. In some embodiments, the method further comprises identifying one or more active haptic senders, identifying a haptic receiver for a given body component, determining a distance between the given body component and any one of the one or more haptic senders that are associated with the given body component is less than a threshold value, and triggering the haptic receiver based on the determination of the distance. In some embodiments, determining the distance between the given body component and any one of the one or more active haptic senders associated with the given body component further comprises determining positional data of the given body component for a trainee user based on the second motion data. In some embodiments, the method further comprises comparing positional data of at least the given body component with positional data of the one or more haptic senders. In some embodiments, the visual guidance data comprises a virtual trainer demonstrating performance of sample motions for a second user associated with the second client computing device to follow. In some embodiments, the visual guidance data comprises a semi-transparent figure for a second user associated with the second client computing device to align bodies with a first user associated with the first client computing device.

According to one embodiment, the system comprises an application server configured to generate visual guidance data based on first motion data received from a trainer module, transmit the visual guidance data to a trainee module, receive second motion data from the trainee module, generate haptic guidance data based on a comparison of the second motion data with the first motion data, and transmit the haptic guidance data to the trainee module.

In some embodiments, the first motion data comprises data representative of motion of a first user performing a set of body training tasks. In some embodiments, the haptic guidance data comprises positive feedback representative of relatively accurate motion with respect to an exercise or activity based on the comparison of the second motion with the first motion data. In some embodiments, the haptic guidance data comprises feedback on one or more of body positioning, muscle activation, or movement pacing and control. In some embodiments, the data processing server is further configured to identify one or more active haptic senders, identify a haptic receiver for a given body component, determine a distance between the given body component and any one of the one or more haptic senders that are associated with the given body component is less than a threshold value, and trigger the haptic receiver based on the determination of the distance.

According to one embodiment, the one or more non-transitory computer-readable storage media including instructions that, when executed by one or more processors, cause the one or more processors to generate visual guidance data based on first motion data received from a first client computing device, transmit the visual guidance data to a second client computing device, receive second motion data from the second client computing device, generate haptic guidance data based on a comparison of the second motion data with the first motion data, and transmit the haptic guidance data to the second client computing device.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
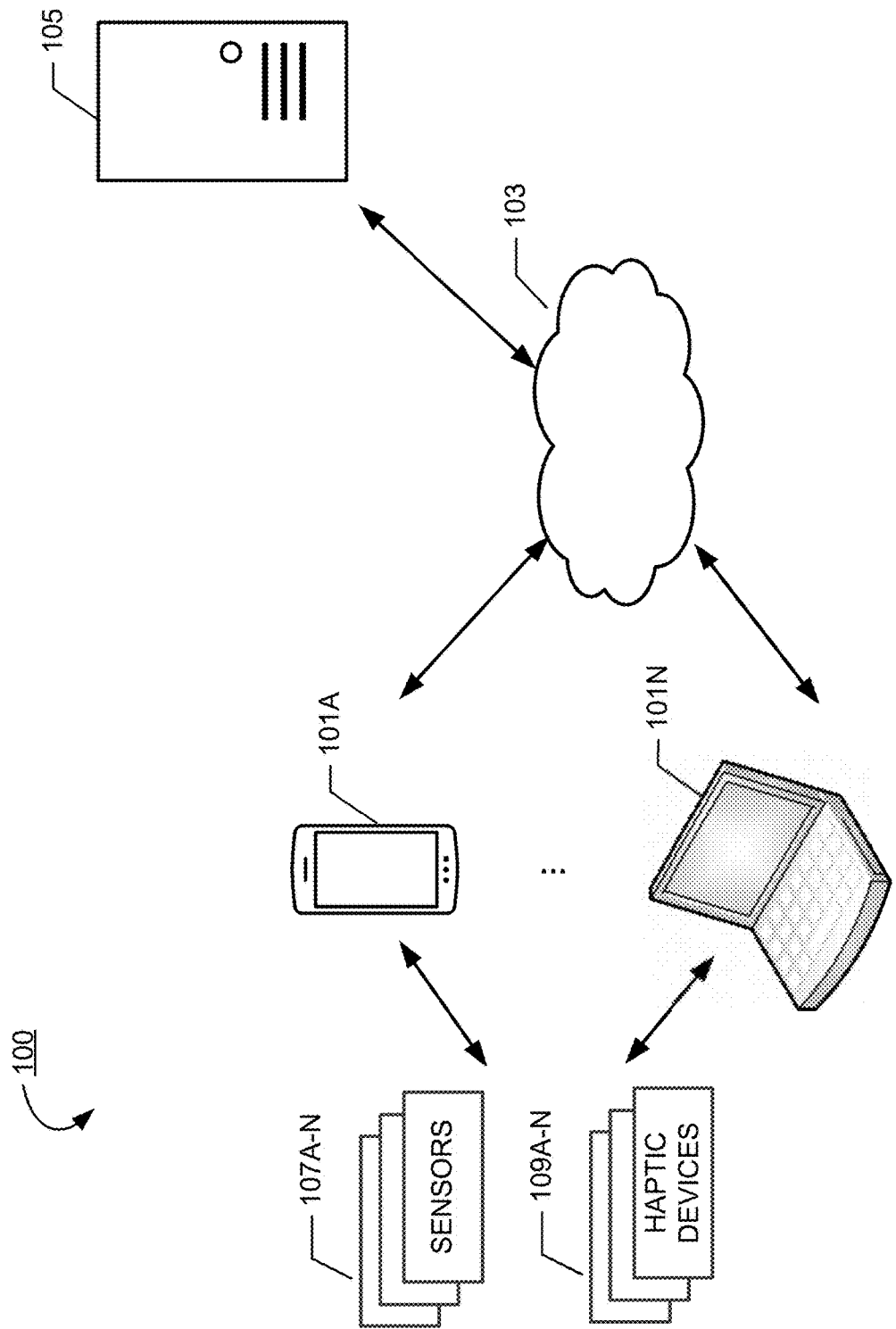
FIG. 1 illustrates an example motor training system in accordance with some example embodiments described herein.

Various embodiments of the present disclosure now will be described more fully hereinafter with reference to the accompanying drawings, in which some, but not all embodiments of the disclosure are shown. Indeed, the disclosure may be embodied in many different forms and should not be construed as limited to the embodiments set forth herein. Rather, these embodiments are provided so that this disclosure will satisfy applicable legal requirements. The term "or" is used herein in both the alternative and conjunctive sense, unless otherwise indicated. The terms "illustrative," "example," and "exemplary" are used to be examples with no indication of quality level. Like numbers refer to like elements throughout.

General Overview and Exemplary Technical Improvements

The present disclosure provides a system and method for providing visual and haptic guidance cues in trainer-to-trainee interactions. In some embodiments, a haptic-based sensation transfer system is provided that migrates haptic and kinematic feeling of movements associated with gym training or any other physical activity from a trainer to a trainee. Sensation transfer may refer to a human motor skill training paradigm that migrates the human motor experience and sensation from one person to another person. According to various embodiments of the present disclosure, sensation transfer may realized through a whole-body hapto-tactile system in an immersive virtual environment. The disclosed system may enable remote and distributed training for motions that need special attention. Motions performed by a trainer can be captured and recorded with motion tracking devices and techniques.

According to various embodiments of the present disclosure, a visual and haptic guidance system may transfer physical sensations from trainer to trainee within an immersive VR environment. As such, the transfer of physical sensations may enable migration of human motor experience from a trainer to a trainee. The visual and haptic guidance system may also generate haptic feedback of different patterns depending on how a trainee follows the motion trajectories of a trainer. Data may also be collected from VR interaction logs to enable real-time assessment of the trainee's motions. The trainee's performance (i.e., accuracy of the motion) can be evaluated with the summed average of spatial discrepancies between the trainee's motions and the trainer's motions.

In some embodiments, the visual and haptic guidance system comprises a trainer module, a trainee module, and a data processing server. The trainer module may be configured to collect and model motion from a trainer. The data processing server may process the collected motion data and configure the motion in VR, while instantiating visual and haptic guidance to assemble the trainer's motion data. The dataset may then be transferred to the trainee module where trainees can follow the motion in VR with visual and haptic sensations.

In some embodiments, motion data of the trainer may be collected via inertia measurement units (IMUs), electromyography (EMG) sensors, and/or infrared light-based motion tracking sensors. Motion tracked by the sensors may be projected on and reproduced on the trainee's body via haptic media. As an example, a VR headset, motion tracking devices, and haptic devices may be used to digitalize sensorimotor experiences for transfer to a trainee user via visual and haptic stimulation. The VR headset may be used to create an immersive virtual environment that enables risk-free body workout training for various scenarios. A whole-body tracking device may be used to capture a trainer's whole-body kinematics which may be streamed into a VR environment. Haptic devices may generate haptic guidance to transfer sensation of the trainer associated with the use of different muscle groups and the feeling of touching and resistance in body workout movement, such as lifting a weight. Digitalized body motions of the trainer may be reconstructed in VR to create an egocentric training experience for the trainee. A virtual training environment may be simulated to transfer the human motor experience of the trainer with visual and haptic guidance corresponding to real-time motor performance of the trainee. This sensation transfer approach can also be used for transferring teachings from trainer to trainee in learning any new task, such as a new operation or a new tool.

Exemplary Technical Implementation of Various Embodiments

Embodiments of the present disclosure may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established, or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid-state card (SSC), solid-state module (SSM)), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises a combination of computer program products and hardware performing certain steps or operations.

Embodiments of the present disclosure are described with reference to example operations, steps, processes, blocks, and/or the like. Thus, it should be understood that each operation, step, process, block, and/or the like may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically configured machines performing the steps or operations specified in the block diagrams and flowchart illustrations. Accordingly, the block diagrams and flowchart illustrations support various combinations of embodiments for performing the specified instructions, operations, or steps.

Exemplary System Architecture

Referring now to FIG. 1, an example diagram illustrating an example motor training system 100 in accordance with some example embodiments described herein is provided. As shown in FIG. 1, the example motor training system 100 comprises apparatuses, devices, and components such as, but not limited to, one or more client computing devices 101A-N, a data processing server 105 in a remote computing platform, and one or more networks 103.

In some embodiments, each of the components of the example motor training system 100 may be in electronic communication with, for example, one another over the same or different wireless or wired networks 103 including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

For example, the one or more client computing devices 101A-N, and the data processing server 105 in the remote computing platform may be in electronic communication with one another to exchange data and information. As described herein, a given one of the client computing devices 101A-N may receive motion data from one or more sensors 107A-N, respectively. Sensors 107A-N may comprise IMUs, EMG sensors, infrared light sensors, virtual reality trackers, or other motion tracking devices. In some embodiments, the given one of the client computing devices 101A-N may transmit motion data from the one or more sensors 107A-N to the data processing server 105 in the remote computing platform for analysis.

In some embodiments, the data processing server 105 in the remote computing platform may receive the motion data from the given one of the client computing devices 101A-N and generate visual guidance data and haptic feedback data based at least in part on the motion data. The data processing server 105 may transmit the visual guidance data and haptic feedback data to at least a second one of the one or more client computing devices 101A-N. The at least second one of the one or more client computing devices 101A-N may process the visual guidance data and haptic feedback data for rendering and output on the one or more client computing devices 101A-N and haptic devices 109A-N. In some embodiments, the at least second one of the one or more client computing devices 101A-N may generate renderings and activate haptic devices based at least in part on the visual guidance data and haptic feedback data in accordance with various example methods described herein.

Figure 2:
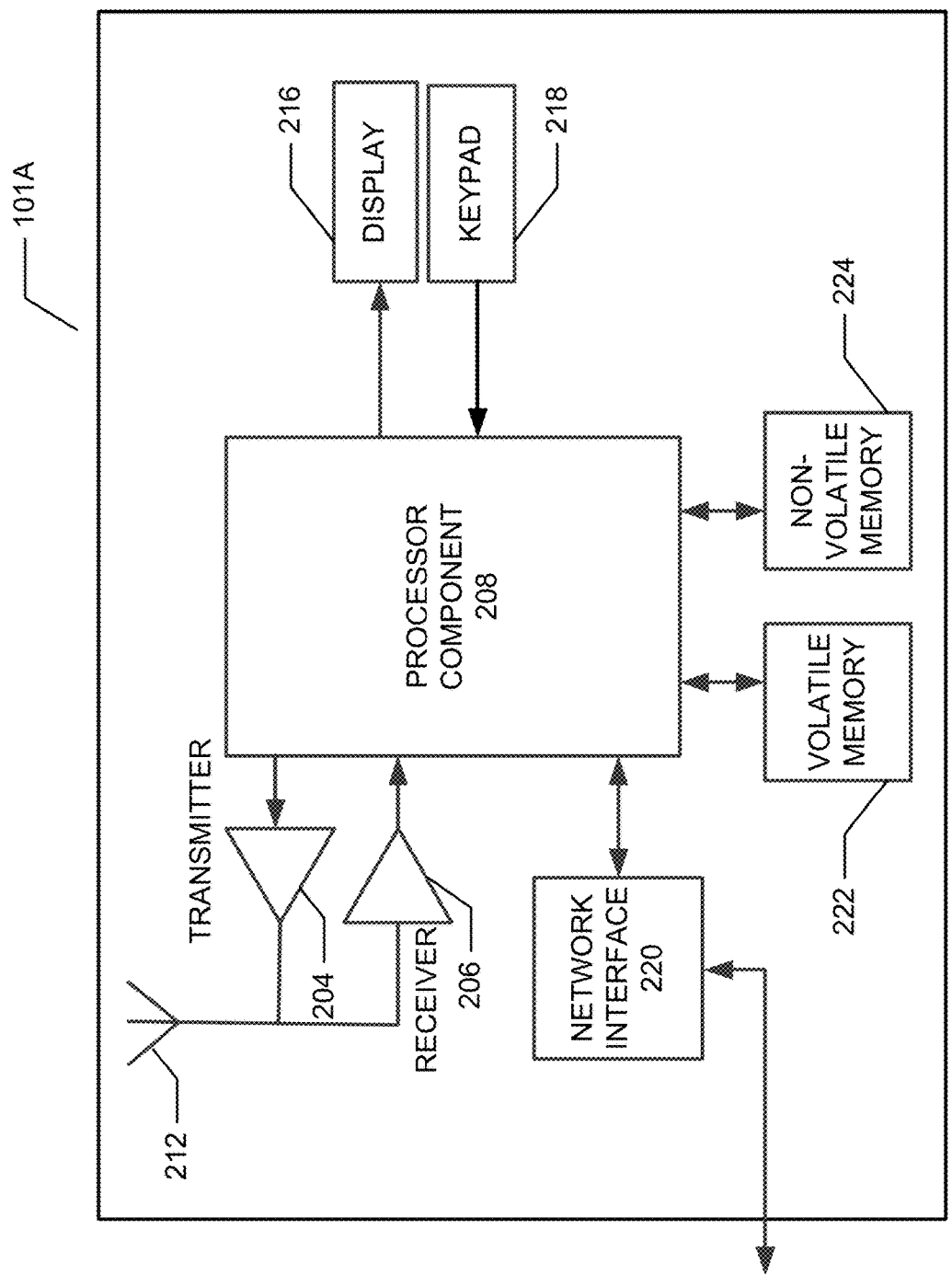
FIG. 2 is an example schematic representation of an example client computing device in accordance with some example embodiments described herein.

Referring now to FIG. 2, an example schematic representation of an example client computing device in accordance with some example embodiments described herein is provided. For example, FIG. 2 provides an illustrative schematic representative of one of the client computing devices 101A-N that can be used in conjunction with embodiments of the present disclosure. In some embodiments, as illustrated in FIG. 2, the client computing device 101A includes an antenna 212, a transmitter 204 (e.g., radio), a receiver 206 (e.g., radio), and a processor component 208 that provides signals to and receives signals from the transmitter 204 and receiver 206, respectively. The signals provided to and received from the transmitter 204 and the receiver 206, respectively, may include signaling information/data in accordance with an air interface standard of applicable wireless systems to communicate with various entities, such as a data processing server 105, another one of client computing devices 101B-N, an example monitoring system, and/or the like. In this regard, the client computing device 101A may be capable of operating with one or more air interface standards, communication protocols, modulation types, and access types. More particularly, the client computing device 101A may comprise a network interface 220 and may operate in accordance with any of a number of wireless communication standards and protocols. In a particular embodiment, the client computing device 101A may operate in accordance with multiple wireless communication standards and protocols, such as GPRS, UMTS, CDMA1900, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the client computing device 101A can communicate with various other entities using Unstructured Supplementary Service data (USSD), Short Message Service (SMS), Multimedia Messaging Service (MMS), Dual-Tone Multi-Frequency (DTMF) Signaling, Subscriber Identity Module Dialer (SIM dialer), and/or the like. The client computing device 101A can also download changes, add-ons, and updates, for instance, to its firmware, software (e.g., including executable instructions, applications, program modules), and operating system.

The client computing device 101A may also comprise a user interface comprising one or more user input/output interfaces (e.g., haptic devices 109A-N in communication with a processor component 208, a display 216 and/or speaker/speaker driver coupled to a processor component 208, and a keypad 218 and/or touch screen, keyboard, mouse, and/or microphone coupled to a processor component 208). For example, the user output interface may be configured to provide an application, browser, user interface, dashboard, webpage, and/or similar words used herein interchangeably executing on and/or accessible via the client computing device 101A to cause display or audible presentation of information/data and for user interaction therewith via one or more user input interfaces. The user output interface may be updated dynamically from communication with the data processing server 105 and/or with another one of client computing devices 101B-N. The user input interface can comprise any of a number of devices allowing the client computing device 101A to receive data, such as a keypad 218 (hard or soft), a touch display, voice/speech or motion interfaces (e.g., via haptic devices 109A-N), scanners, readers, or other input device. In embodiments including a keypad 218, the keypad 218 can include (or cause display of) the conventional numeric (0-9) and related keys (#, *), and other keys used for operating the client computing device 101A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the client computing device 101A can collect information/data, user interaction/input, and/or the like.

According to various embodiments of the present disclosure a given one of haptic devices 109A-N may comprise one or more vibration components in communication with processor component 208, e.g., via network interface 220 or antenna 212. In some embodiments, sensors 107A-N and haptic devices 109A-N may communicate with processor component 208 through wireless protocols, such as Bluetooth or Wi-Fi. In some embodiments, the processor component 208 may also communicate with sensors 107A-N and haptic devices 109A-N using wired communication protocols, such as universal asynchronous receiver/transmitter (UART), serial peripheral interface (SPI), or inter-integrated circuit (I2C). According to various embodiments of the present disclosure, the processor component 208 may be programmed based on different exercise and motion needs, providing versatility and adaptability. The processor component 208 may be configured to receive data from sensors 107A-N, such as position, speed, and muscle activation features, and use the data to generate vibration patterns via haptic devices 109A-N.

The client computing device 101A can also include volatile storage or memory 222 and/or non-volatile storage or memory 224, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the client computing devices 101A-N.

Figure 3:
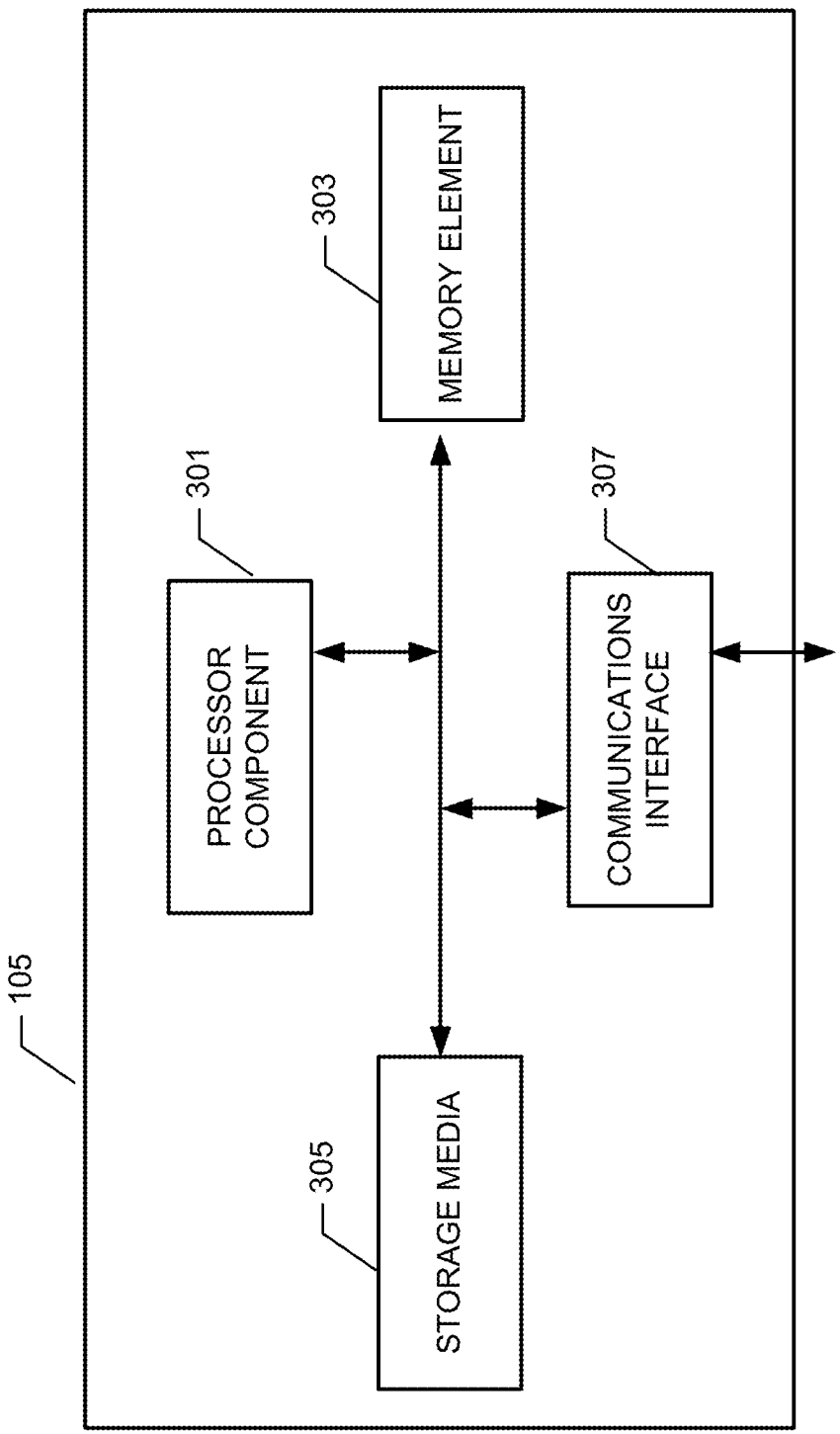
FIG. 3 is an example schematic representation of an example remote computing server of an example remote computing platform in accordance with some example embodiments described herein.

Referring now to FIG. 3, an example schematic representation of an example data processing server 105 in an example remote computing platform in accordance with some example embodiments described herein. In some embodiments, the example remote computing platform may be a cloud computing platform, and the example remote computing server may be a cloud computing server.

As indicated, in some embodiments, the data processing server 105 may include one or more network and/or communications interface 307 for communicating with various computing entities, such as by communicating data, content, information, and/or similar terms used herein that can be transmitted, received, operated on, processed, displayed, stored, and/or the like. For instance, the data processing server 105 may communicate with one or more client computing devices 101A-N.

As shown in FIG. 3, in one embodiment, the data processing server 105 may include or be in communication with one or more processor components (for example, processor component 301) (also referred to as processor components, processing circuitry, and/or similar terms used herein interchangeably) that communicate with other elements within the data processing server 105 via a bus, for example, or network connection. As will be understood, the processor component 301 may be embodied in a number of different ways. For example, the processor component 301 may be embodied as one or more complex programmable logic devices (CPLDs), microprocessor components, multi-core processor components, co-processing entities, application-specific instruction-set processor components (ASIPs), and/or controllers. Further, the processor component 301 may be embodied as one or more other processing devices or circuitry. The term circuitry may refer to an entirely hardware embodiment or a combination of hardware and computer program products. Thus, the processor component 301 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processor component 301 may be configured for a particular use or configured to execute instructions stored in volatile or non-volatile media or otherwise accessible to the processor component 301. As such, whether configured by hardware or computer program products, or by a combination thereof, the processor component 301 may be capable of performing steps or operations according to embodiments of the present disclosure when configured accordingly.

In one embodiment, the data processing server 105 may further include or be in communication with volatile media (also referred to as volatile storage, memory, memory storage, memory circuitry, and/or similar terms used herein interchangeably). In one embodiment, the volatile storage or memory may also include one or more memory elements 303 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory element 303 may be used to store at least portions of the databases, database instances, database management system entities, data, applications, programs, program modules, scripts, source code, object code, byte code, compiled code, interpreted code, machine code, executable instructions, and/or the like being executed by, for example, the processor component 301 as shown in FIG. 3. Thus, the databases, database instances, database management system entities, data, applications, programs, program modules, scripts, source code, object code, byte code, compiled code, interpreted code, machine code, executable instructions, and/or the like may be used to control certain aspects of the operation of the data processing server 105 with the assistance of the processor component 301 and operating system.

In one embodiment, the data processing server 105 may further include or be in communication with non-volatile media (also referred to as non-volatile storage, memory, memory storage, memory circuitry, and/or similar terms used herein interchangeably). In one embodiment, the non-volatile storage or memory may include one or more non-volatile storage or storage media 305 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or storage media 305 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Storage media 305 may also be embodied as a data storage device or devices, as a separate database server or servers, or as a combination of data storage devices and separate database servers. Further, in some embodiments, storage media 305 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery prediction system may be stored.

As indicated, in one embodiment, the data processing server 105 may also include one or more network and/or communications interface 307 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data processing server 105 may be configured to communicate via wireless external communication networks using any of a variety of protocols, such as general packet radio service (GPRS), Universal Mobile Telecommunications System (UMTS), Code Division Multiple Access 1900 (CDMA1900), CDMA1900 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), Institute of Electrical and Electronics Engineers (IEEE) 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The data processing server 105 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the remote computing server's components may be located remotely from components of other remote computing servers, such as in a distributed system. Furthermore, one or more of the components may be aggregated and additional components performing functions described herein may be included in the data processing server 105. Thus, the data processing server 105 can be adapted to accommodate a variety of needs and circumstances.

Example Visual and Haptic Guidance System

Various embodiments of the present disclosure describe components, apparatuses, and systems, and/or the like for guiding users through gym workouts by monitoring user motion kinematics and providing real-time feedback on body positioning, muscle engagement, or movement pacing and control. The disclosed embodiments may be used to improve workout technique and effectiveness by transferring visual and haptic effects of motions, developed by a trainer, to a trainee to teach users on proper muscle group activation and exercise form.

Figure 4:
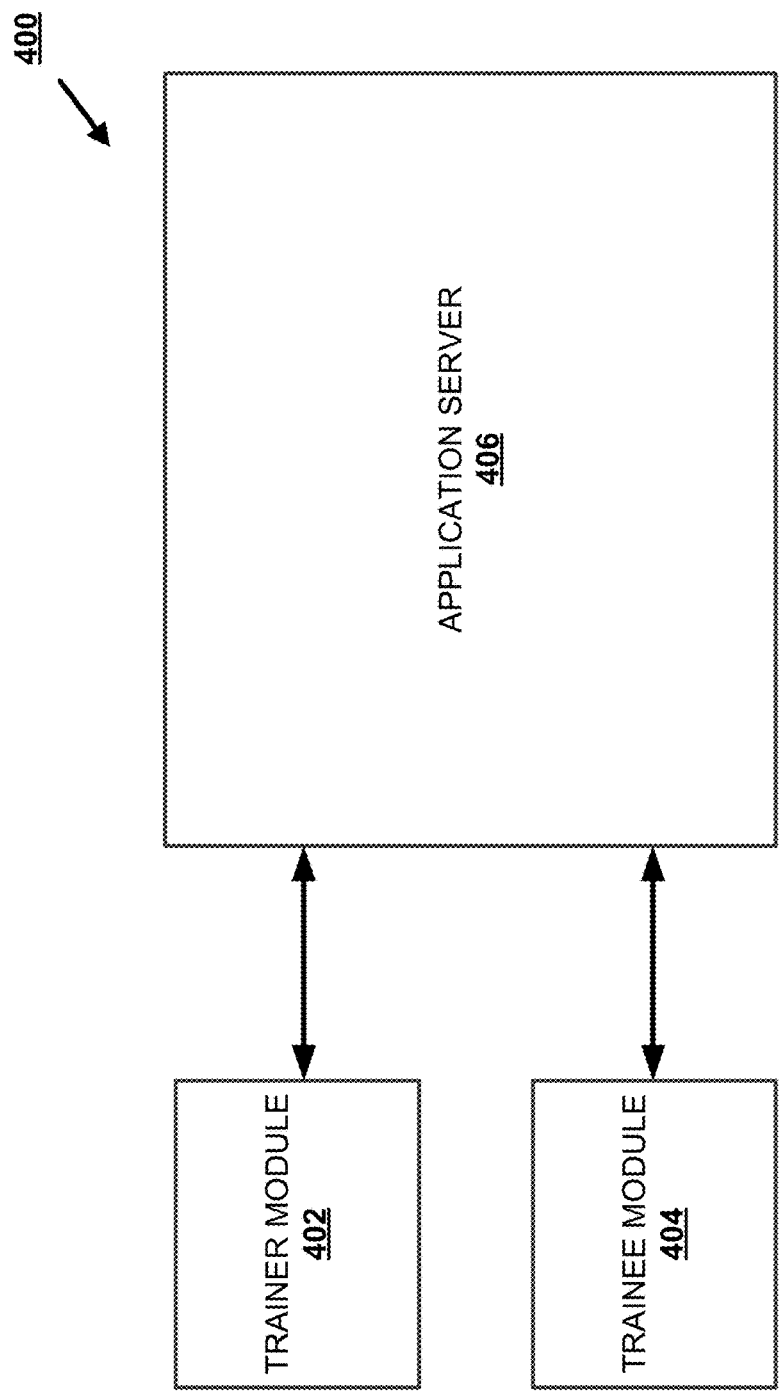
FIG. 4 illustrates an exemplary system framework for providing remote human motor training in accordance with some example embodiments described herein.

Referring now to FIG. 4, an example visual and haptic guidance system 400 for providing remote human motor training is illustrated according to some embodiments of the present disclosure. The visual and haptic guidance system 400 comprises a trainer module 402, a trainee module 404, and an application server 406. In some embodiments, trainer module 402 may comprise a client software application or program executed on a first one of client computing devices 101 and trainee module 404 may comprise another client software application or program executed on a second one of client computing devices 101. Application server 406 may comprise an application executing on data processing server 105 configured to service client requests from trainer module 402 and trainee module 404 and enable interaction between trainer module 402 and trainee module 404. The visual and haptic guidance system 400 may comprise any number of trainer module 402 and trainee module 404 and is not limited to the illustrated embodiment.

According to various embodiments of the present disclosure, the visual and haptic guidance system 400 may be used to effectively target the appropriate muscle groups and body areas during a workout for various exercises. Haptic devices may be used with visual and haptic guidance system 400 to provide kinematic and kinesthetic feedback about a user's current motion based on a specific exercise or motion and motion data captured by sensor devices. Visual and haptic guidance system 400 may monitor the user's body posture and muscle activation using sensors and provide different patterns of augmented feedback to users via haptic devices. The feedback pattern can be adapted to different exercises by changing the positions of haptic devices.

In some embodiments, the visual and haptic guidance system 400 may be used with detachable haptic devices (e.g., haptic devices 109A-N) that allow users to move and adjust the placement of vibrating modules on their body. Such variability of haptic device placement allows for tailoring visual and haptic guidance system 400 to different exercises, as it enables users to position vibrating modules on specific muscle groups or body areas involved in each movement. In some embodiments, the visual and haptic guidance system 400 may provide vibration patterns tailored to each exercise, providing targeted feedback on aspects such as body positioning, muscle activation, or movement pacing and control. Vibration patterns can be adjusted in intensity and duration to suit the user's fitness level and preferences. A user can adjust the haptic devices' layout, sensitivity, and feedback levels to provide optimal performance for each specific exercise.

The following provides example haptic device configurations for specific exercises:

Squats: Trainee users can place vibrating modules on their glutes, quadriceps, and/or lower back to receive feedback on proper muscle engagement and body positioning throughout a squat.

Bicep curls: Vibrating modules can be positioned on the biceps and/or forearm to provide feedback on muscle activation and ensure that a trainee user is not compensating with other muscle groups, such as the shoulders or back.

Planks: By placing vibrating modules on the abdominal muscles, lower back, and/or shoulders, trainee users can receive feedback on maintaining proper core activation and body alignment during a plank.

Deadlifts: The haptic devices can provide feedback on hip hinge and lower back positioning by delivering vibrations to the hips and lower back when a trainee user achieves the correct form. Additionally, vibrating modules on the hamstrings and glutes can be activated to encourage proper muscle engagement.

Bench press: Vibrating modules on the chest, shoulders, and triceps can be programmed to activate in sequence, providing guidance on proper muscle activation and movement control during the exercise.

Yoga poses: The haptic devices can provide feedback on body alignment, balance, and muscle engagement during various yoga poses by activating vibrating modules on key body areas, such as the hips, shoulders, and core.

In some embodiments, the visual and haptic guidance system 400 can also be applied in various rehabilitation settings to assist patients in regaining strength, mobility, and function. The following provides some example applications for rehabilitation:

Stroke Recovery: Patients recovering from a stroke often struggle with muscle weakness, coordination, and sensory loss. The visual and haptic guidance system 400 can be customized to provide feedback on proper movement patterns, muscle activation, and body positioning during targeted exercises. This can help stroke survivors regain motor function, improve balance, and relearn everyday tasks.

Physical Therapy for Orthopedic Injuries: Patients recovering from orthopedic injuries, such as fractures, joint replacements, or ligament tears, can benefit from using the visual and haptic guidance system 400 during their physical therapy sessions. The system can provide guidance on proper form and alignment during exercises, ensuring that patients do not compensate with other muscle groups or develop improper movement patterns. This can facilitate a faster and more effective recovery.

Spinal Cord Injury Rehabilitation: For patients with spinal cord injuries, the visual and haptic guidance system 400 can be customized to provide feedback on muscle activation and body positioning during exercises that target specific muscle groups. This can help patients relearn how to engage and control their muscles, improving their mobility, independence, and quality of life.

Neuromuscular Disorder Rehabilitation: Individuals with neuromuscular disorders, such as Parkinson's disease or multiple sclerosis, can benefit from using the visual and haptic guidance system 400 during rehabilitation exercises. The visual and haptic guidance system 400 system can provide feedback on muscle activation, movement control, and body positioning, helping patients improve their strength, coordination, and balance.

Gait Retraining: Patients who need to relearn how to walk due to injury, surgery, or neurological conditions can use the visual and haptic guidance system 400 during gait retraining exercises. The haptic devices can provide real-time feedback on proper foot placement, weight distribution, and stride length, helping patients develop a more efficient and stable walking pattern.

Postural Correction: The visual and haptic guidance system 400 can be used to help patients with postural issues, such as kyphosis, scoliosis, or rounded shoulders, improve their body alignment and posture. By providing feedback on proper spine alignment and muscle activation, the haptic devices can guide patients in strengthening their core muscles and maintaining a more balanced and upright posture.

Fall Prevention: Elderly patients or those with balance issues can benefit from using the visual and haptic guidance system 400 during balance training exercises. The haptic devices can provide feedback on body positioning and weight distribution, helping patients develop better balance, proprioception, and overall stability, reducing their risk of falls.

To simplify the customization process for users, the visual and haptic guidance system 400 may provide pre-set configurations for common exercises. The pre-set configurations can be selected on a user interface accessed by using a client computing device to ensure that vibrating modules are positioned and programmed correctly for each exercise. Users can also create and save their custom configurations for specific exercises or workout routines via the user interface. The visual and haptic guidance system 400 may further comprise a configuration decision support feature that utilizes musculoskeletal analysis to optimize the configuration of vibrating modules on haptic devices. Such a feature may help users determine the most effective vibrating module placements and settings for their specific exercises, body types, and rehabilitation goals. In some embodiments, the user interface incorporates a musculoskeletal model that takes into account the user's body dimensions, joint ranges of motion, and muscle activation patterns. The musculoskeletal model can be used to simulate the biomechanics of various exercises and estimate the optimal vibrating module placements for providing effective haptic feedback.

Example Configuration Decision Support

Users may provide their body measurements, such as height, weight, and limb lengths, as well as any relevant medical or injury history to haptic guidance system 400 via a user interface on trainee module 404. Body measurement information may be used to personalize a musculoskeletal model and tailor vibrating module configuration recommendations to an individual user.

For each selected exercise, the haptic guidance system 400 may analyze associated muscle groups, movement patterns, and biomechanics, using the personalized musculoskeletal model. This analysis may identify key areas where haptic feedback can be most effective in guiding proper form, muscle activation, and body positioning. Based on the exercise analysis, the haptic guidance system 400 may generate recommendations for the optimal placement and configuration of the vibrating modules on the haptic devices. These recommendations may ensure that haptic feedback targets appropriate muscle groups and body areas, maximizing the effectiveness of guidance provided during the exercise.

In addition to recommending vibrating module placements, the haptic guidance system 400 can also optimize vibration patterns for each exercise, such as adjusting the intensity, duration, and sequencing of vibrations to provide the most effective feedback for muscle activation, movement pacing, and form correction. As users progress through their workouts and rehabilitation, the haptic guidance system 400 can continuously adapt vibrating module placements and settings based on changing needs and goals. This ensures that the haptic guidance system 400 remains effective and supportive throughout a user's entire fitness journey.

In some embodiments, the haptic guidance system 400 can also be integrated with existing physical therapy or rehabilitation programs, allowing healthcare professionals to fine-tune the haptic guidance system 400 settings for their patients based on their specific needs, goals, and progress.

In some embodiments, the haptic guidance system 400 may be programmed with feedback patterns tailored to specific exercises, such as squats, lunges, or push-ups. Feedback patterns may provide users with information on proper body positioning, muscle activation, or movement pacing and control. For example, haptic devices can generate vibrations to indicate correct alignment of body parts, such as maintaining a straight back or keeping knees above ankles during a squat. By integrating sensors, such as EMG sensors, the haptic guidance system 400 can provide feedback on whether the user is engaging appropriate muscles during the exercise. The haptic guidance system 400 can also help users maintain a consistent tempo and ensure smooth, controlled movements by providing timed vibrations as cues.

Example Trainer Module

The trainer module 402 may be configured to generate training definitions for certain exercises or activities via capturing of motion data associated with a trainer user, such as a gym tutor, teacher, therapist, specialist, instructor, or expert practitioner, during performance of the certain exercises or activities. In some embodiments, trainer module 402 is communicatively coupled to one or more sensors (e.g., sensors 107A-N) worn by the trainer user and motion data may be received by the trainer module 402 from the one or more sensors. The one or more sensors may comprise devices, such as IMUs and EMG sensors, used to accurately assess body position, movement, and muscle activation during exercises. The motion data may be transmitted from the trainer module 402 to the application server 406 during a recording phase or training session. During the recording phase or training session, trainer module 402 may generate instructions for the trainer user to perform, such as a set of body training tasks in a defined tracking space. Motion data associated with the instructions may be received by the application server 406 and extracted into frames for generating visual guidance data and haptic feedback data that can be transferred and conveyed to trainee module 404.

A training session may be defined by the type of motions and the model of the body workout. A variety of motions can be collected and assembled from the motion data. In some embodiments, attributes of motions are extracted from sensors 107A-N based on correlation between components, position, time, time series spatial position, rotation, scale, and/or reference. As such, whole-body motion kinematics data can be collected via sensors deployed at proper positions on the trainer may record the whole-body motion kinematics at a given frequency, such as 90 Hz.

Example Trainee Module

Trainee module 404 may be configured to receive visual guidance data and haptic feedback data from application server 406 (e.g., based on motion data received from trainer module 402) to provide a trainee user, such as a student, apprentice, or learner, with motion guidance and feedback. Visual guidance data may be delivered in the form of a virtual trainer comprising a VR avatar demonstrating the performance of sample motions for the trainee user to follow. The trainee user can observe the motions from multiple view perspectives (e.g., the third-person view and the first-person view) and follow along.

The trainee module 404 may also be communicatively coupled to one or more sensors (e.g., sensors 107A-N) and haptic devices (e.g., haptic devices 109A-N). The one or more sensors may comprise devices, such as IMUs and EMG sensors. IMUs may comprise accelerometers, gyroscopes, and magnetometers, and can be used to track body movements and orientations during exercises. Data collected by IMUs may be used to determine feedback on proper form. An EMG sensor may comprise a device that can measure muscle activity, which may be used to determine feedback on proper muscle engagement during exercises to activate correct muscles and improve exercise technique.

In some embodiments, trainee module 404 further comprises a musculoskeletal evaluation module that is configured to determine motion correctness and musculoskeletal load based on a comparison of motion data received from the one or more sensors coupled to the trainee module 404 and motion data of a trainer module, which may be received from application server 406. In some embodiments, trainee module 404 may transmit the motion data received from the one or more sensors coupled to the trainee module 404 to application server 406 to receive instructions for generating real-time responses in the form of haptic feedback by activating the haptic devices coupled to the trainee module 404 based on the motion correctness and musculoskeletal load.

In some embodiments, trainee module 404 further comprises a user interface for connecting trainee module 404 with one or more sensors and haptic devices and allowing trainee users to monitor, configure, and control settings. In some embodiments, the user interface comprises a dashboard configured to display an overview of the trainee user's current haptic system settings, such as a selected exercise, vibration intensity, and location of active vibrating modules. In some embodiments, the user interface further comprises a library of pre-set exercise configurations, allowing trainee users to select and load appropriate settings for their chosen workout. Trainee users may create and save custom configurations, tailoring the visual and haptic guidance system to their specific needs and preferences. In some embodiments, the user interface further comprises vibration configurations for allowing trainee users to adjust intensity, duration, and pattern of vibrations for each exercise to fine-tune haptic feedback based on individual sensitivity and fitness level. Tuning the visual and haptic configurations can also provide different training conditions.

In some embodiments, the user interface is configured to generate sensor data visualization comprising real-time sensor data, such as muscle activation (e.g., from EMG sensors) and body movement (e.g., from IMUs). Data visualization can be presented in graphical or numerical formats, enabling trainee users to monitor their performance and progress during exercises. In some embodiments, the user interface comprises progress tracking and analytics features for tracking and storing data from a trainee user's workout sessions, providing insights into their performance, technique improvements, and areas for further development. Trainee users can review their workout history, set goals, and track their progress over time. In some embodiments, the user interface comprises access to tutorials and guided workouts provided by application server 406 including instructional videos, guides, and animations to help trainee users learn proper exercise techniques and form. For example, the user interface may allow a trainee user to access guided workout routines that utilize the visual and haptic guidance system's feedback capabilities to provide step-by-step instructions and real-time corrections. In some embodiments, the user interface comprises one or more features for connecting to third-party fitness applications and devices, allowing trainee users to integrate visual and haptic guidance system data with their existing fitness ecosystem. In some embodiments, the user interface comprises a feature for supporting multiple user profiles, enabling different trainee users to customize and save their preferred visual and haptic guidance system settings. This feature is particularly useful for shared devices or in settings such as gyms and rehabilitation centers.

Example Application Server

In some embodiments, motion data from trainer module 402 may be received and processed by a game-engine-based application server 406. The application server 406 may be configured to record and reconstruct visual and haptic characteristics from raw motion data received from trainer module 402 to generate visual guidance data and haptic feedback data for conveying the visual and haptic characteristics to trainee module 404 during live training sessions, tutorials, or guided workouts.

Figure 5:
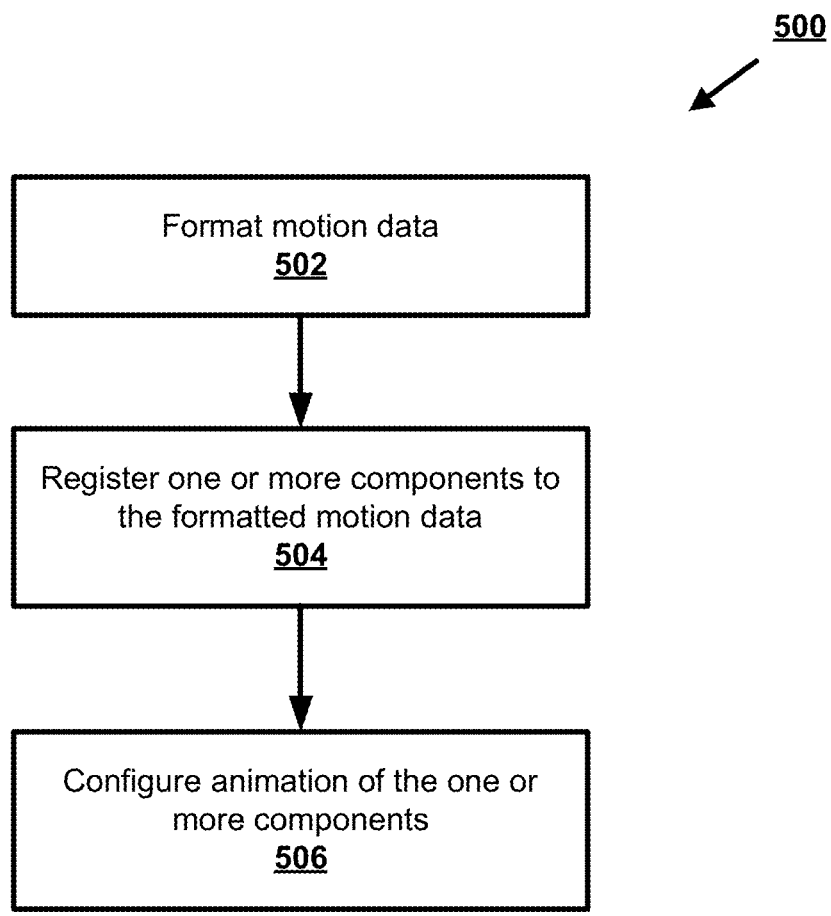
FIG. 5 depicts an example process for generating visual guidance data in accordance with some example embodiments described herein.

FIG. 5 depicts an example process for generating visual guidance data. In particular, process 500 comprises steps for re-constructing motion data from the trainer module 402 into animations rendered with a VR avatar. The process 500 includes example operations that may be performed by the data processing server 105, and the data processing server 105 comprises means, such as processor component 301, memory element 303, communications interface 307, and/or the like, for performing the example operations.

At step 502, the data processing server 105 formats motion data received from a trainer module (e.g., trainer module 402). The motion data can be transformed to filmbox (FBX) format which is accessible by a game engine, such as Unity Engine, in terms of hierarchy time-series datasets. To establish a connection between FBX files and VR avatars, the FBX files may be configured in the game engine depending on data collection mode.

At step 504, the data processing server registers one or more components to the formatted motion data. Registering the one or more components to the formatted motion data may comprise mapping motion tracking points based on the motion data to a VR avatar.

At step 506, the data processing server configures animation of the one or more components. Configuring the animation may comprise explicitly linking a VR avatar's whole-body motion to the formatted motion data. The FBX files can be accessed as animation documents in the game engine which are further attached to animation controllers to control the virtual avatar's motion. By configuring the animation controller with the motion data, a trainer's motions in the physical world (via trainer module 402) can be reconstructed in VR. The reconstructed animations can then be used as visual guides during training sessions, for example, with trainee module 404.

Figure 6A:
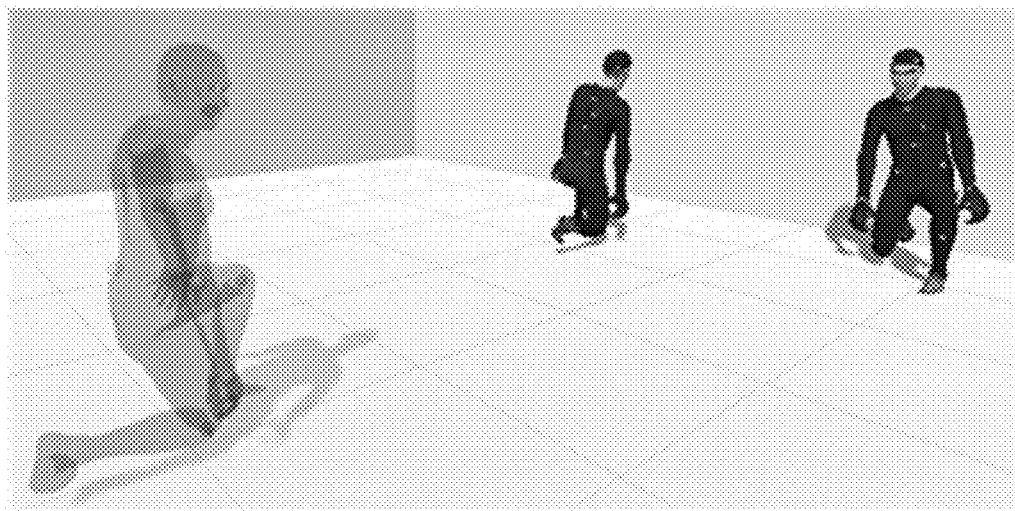
FIGS. 6A and 6B illustrate exemplary visual and haptic guidance in accordance with some example embodiments described herein.
Figure 6B:
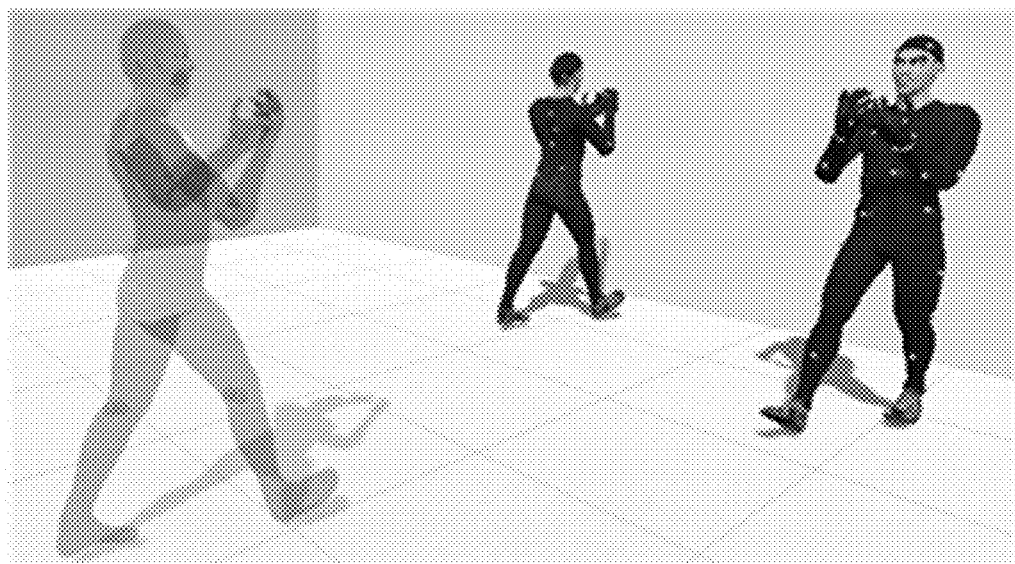

FIGS. 6A and 6B present exemplary visual guidance renderings according to some embodiments of the present disclosure. VR visual guidance may be provided to users at different stages of motion. As depicted in FIGS. 6A and 6B, a semi-transparent figure together with solid figures may comprise visual guidance that the trainee can observe and follow. The semi-transparent figure may comprise a visual for an egocentric trainer user, where the trainee can align their body with the trainer user and observe the trainer user's motion from a first-person view. Solid figures may represent a virtual trainer (e.g., a VR avatar) in the third-person view. Figures within a given k+1 frames window may represent points at which the trainee user receives haptic guidance.

In some embodiments, application server 406 generates haptic feedback data for haptic devices during exercises or activities based on the training definitions created based on motion data from trainer module 402. According to various embodiments of the present disclosure, haptic feedback functions as positive feedback which denotes relatively accurate motion. The accuracy of motion by a trainee may be calculated in real-time and haptic feedback may be generated to reward correct motion. When the trainee repeats the motions accurately, e.g., following the desired motion trajectories and velocities in the 3D body motion space, the haptic devices may provide hapto-tactile feedback, creating an illusion of physical contact, or the feeling of copying the trainer's body motion. When the trainee veers off the track of more than a customized threshold value, the haptic-based sensation may decrease.

Hapto-tactile feedback may be triggered at certain frames of a training session rendered in VR. However, VR refresh rates may not typically be the same as capture frequency of sensor devices. In addition, specific points in space tracked by the sensor devices may not be the same as hapto-tactile points. According to some embodiments of the present disclosure, VR update frequency may be synchronized with motion data points in VR to resample and log spatial-temporal information associated with positions of body components with a desired frequency. For example, the position of the right palm is computed at 90 Hz although the original motion tracking data only had the position of the right wrist at 60 Hz. This resampled data, which specifies the location of the trainer's desired body parts at desired time points, may then be used for a training session with a trainee user. After resampling the points of interest in VR, to create haptic guidance, haptic senders may be instantiated at the trainer's client computing device and haptic receivers may be instantiated at the trainee's client computing device. Hapto-tactile feedback may be triggered once the haptic senders and corresponding haptic receivers collide with each other in space.

Figure 7:
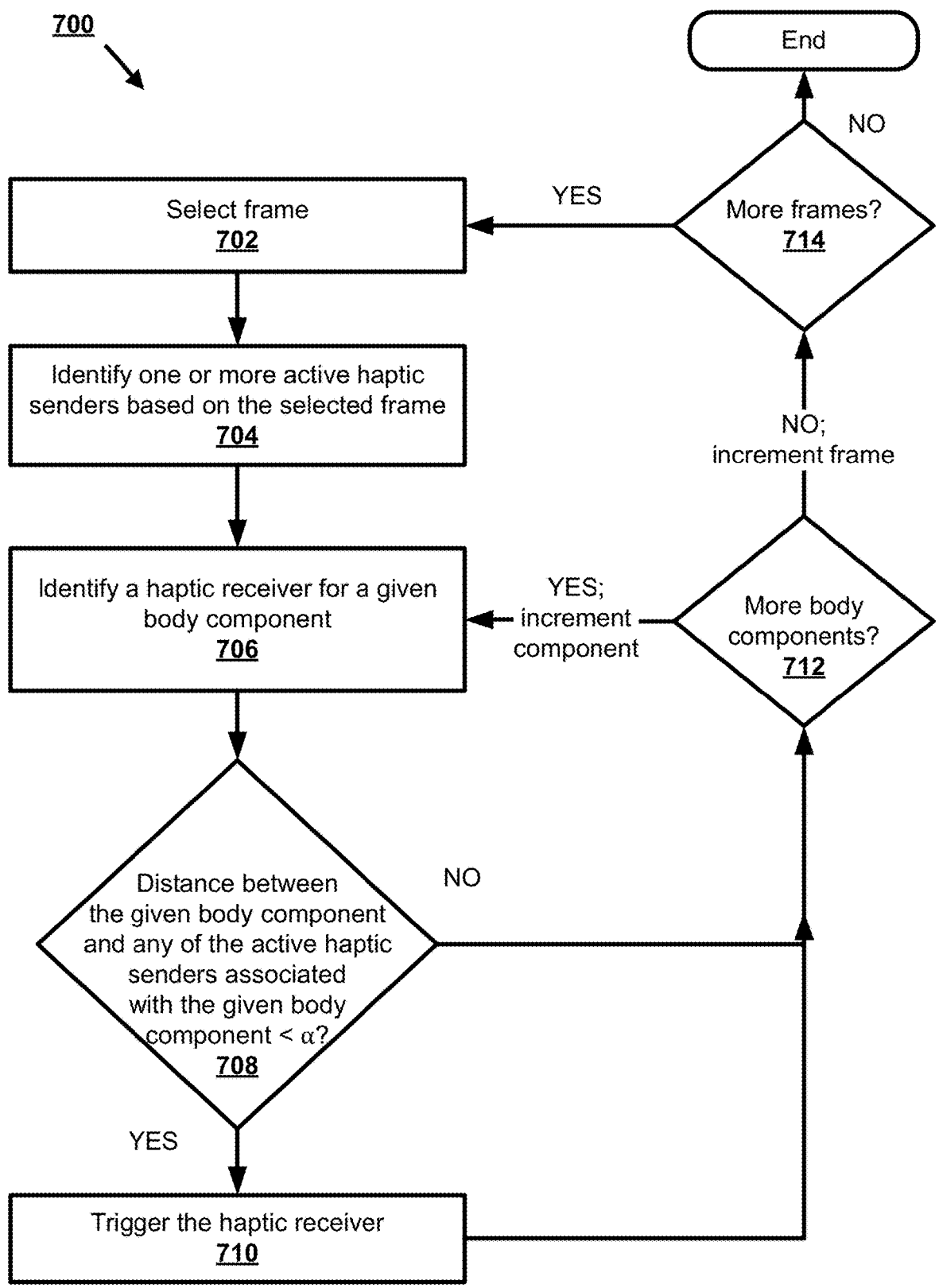
FIG. 7 depicts an example process triggering hapto-tactile feedback during frames of a training session in accordance with some example embodiments described herein.

FIG. 7 depicts an example process triggering hapto-tactile feedback during frames of a training session. The process 700 includes example operations that may be performed by the data processing server 105, and the data processing server 105 comprises means, such as processor component 301, memory element 303, communications interface 307, and/or the like, for performing the example operations.

In some embodiments, at step 702, the data processing server 105 selects a frame of motion data from a trainer module, beginning at a first frame, associated with a training session initiated by a trainee module (e.g., trainee module 404). For example, when a training session is started by the trainee module, each frame of motion data from a trainee module may be subjected to a computational process to determine an appropriate haptic response based on a comparison to motion data received from a trainer module (e.g., trainer module 402). The comparison may be performed on motion data received either during the training session in real-time (e.g., a live training session), or previously saved from a pre-recorded session or tutorial. Training can be conducted under different virtual environments, mimicking various body workout conditions.

In some embodiments, at step 704, the data processing server 105 identifies one or more active haptic senders based on the selected frame. A haptic sender may comprise an identification of a hapto-tactile point on a haptic device associated with one or more body components based on trainer motion data. Identifying the one or more active haptic senders may comprise determining haptic senders based on positional data of body components based on trainer motion data for a certain period or window of frames relative to the selected frame, for example, k frames before and k frames after the current selected frame.

In some embodiments, at step 706, the data processing server 105 identifies a haptic receiver for a given body component. A haptic receiver may comprise an identification of a hapto-tactile point on a trainee haptic device associated with a body component for which haptic feedback may be activated. Identifying the haptic receiver may further comprise extracting from trainee motion data, location coordinates corresponding to the given body component for the selected frame. Trainee motion data may be received and compared with corresponding frames of trainer motion data for an entirety of a duration of the training session. That is, trainee motion data may comprise frames that can be compared in relation to frames of trainer motion data.

Figure 8:
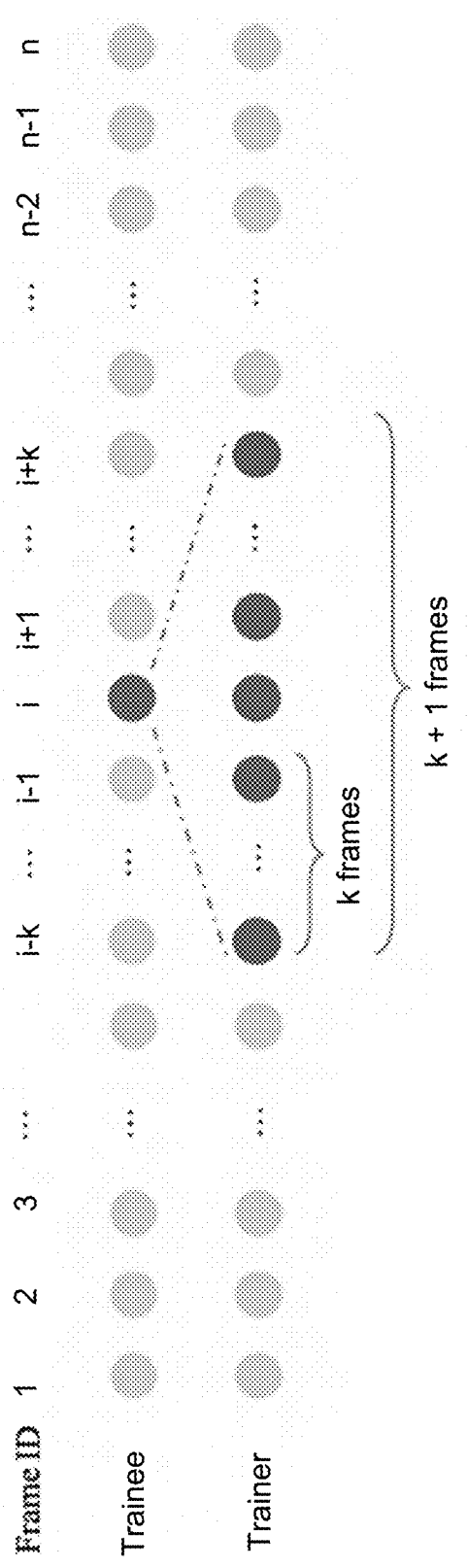
FIG. 8 illustrates exemplary time correspondence between trainee and trainer timelines in accordance with some example embodiments described herein.

FIG. 8 presents a time correspondence between a trainee user's timeline and a trainer's timeline according to an embodiment of the present disclosure. A trainee user's timeline may represent an online process that flows corresponding to real-time. The trainer's timeline may refer to time-series data corresponding to a recording of a trainer's movements during, for example, a training session. As depicted in FIG. 8, haptics may be triggered when haptic receivers (from the trainee) collide with any haptic senders (from the trainer) that are no more than k frames before or after the current frame. The value of k can be customized according to desired tolerance and computational resources. A lower k-value may result in more accurate tracking and a larger k value may result in a larger temporal tolerance, and the parameter k can be set according to both task-needs (e.g., how accurate does the training need to be), and availability of computational resources.

The trainer's effective frames may be non-recurrent in boundary conditions. Depending on the haptic pattern of haptic devices, a single vibration signal might last longer than one frame, which can result in a stacked haptic activation signal. To solve this problem, stacked haptic activation signals may need to be cleared so the signals won't accumulate or cause residual effects. The activation of a trainer's frames can be tuned to be continuous, as shown in FIG. 8, or discrete, for instance, activating once every t frames. According to how sparse the trainer's frames are activated, discrete activation of the trainer's frame might lead to an inaccurate haptic feeling due to some missing frames. The advantage of a discrete pattern is to save computational resources thus lower the hardware burden.

Referring back to FIG. 7, in some embodiments, at step 708, the data processing server 105 determines whether a distance between the given body component of the trainee user and any one of the one or more active haptic senders associated with the given body component is less than a threshold value α. Determining a distance between the given body component and any one of the one or more active haptic senders associated with the given body component may comprise determining positional data of the given body component for the trainee user based on trainee motion data.

In some embodiments, each frame of both the trainee motion data and the trainer motion data may be converted into positional data comprising a matrix $A_i$ of a plurality of 3-dimensional position $\vec{P}$ comprising Cartesian coordinates of m number of interest points as expressed below:

$$A_i = \begin{vmatrix} \vec{P_1} \\ \vec{P_1} \\ \ldots \\ \vec{P_m} \end{vmatrix} = \begin{vmatrix} x_1 & y_1 & z_1 \\ x_2 & y_2 & z_2 \\ \ldots & \ldots & \ldots \\ x_m & y_m & z_m \end{vmatrix} \qquad \text{Equation 1}$$

Positional data of body components where a haptic receiver may be activated can be compared with positional data of active haptic senders. A body component at the selected frame may include a 3-dimensional position $\vec{P}$. In some embodiments, application server 406 may comprise an algorithm that checks whether the distance between $\vec{P}$ of the body component and any active haptic senders with a same body component ID are smaller than a threshold value α. To compensate for differences in height between the trainee and the trainer, a trainer's motion data may be scaled in space according to a trainee's height.

In some embodiments, at step 712, if no active haptic sender is found to be within the threshold value α distance from the given body component, the data processing server 105 continues to check a next body component. For example, the data processing server 105 may iterate through all body components (e.g., interest points) from $\vec{P_1}$ to $\vec{P_m}$ for the selected frame.

In some embodiments, at step 710, if an active haptic sender is found to be within the threshold value α distance from the given body component, the data processing server 105 triggers the haptic receiver. Triggering the haptic receiver may comprise the data processing server 105 generating and sending an instruction to the trainee module to activate a specific haptic component on a haptic device coupled to the trainee module. For example, specific embedded motors may be instructed to vibrate with a pre-determined pattern. The data processing server 105 may trigger hapto-tactile feedback in the selected frame at the corresponding body component and then continue to loop overall body components at step 712.

In some embodiments, at step 714, if all body components have been checked, the data processing server 105 determines if there are more frames to select for processing until a training session finishes.

Example System Operations

Various embodiments of the present disclosure describe steps, operations, processes, methods, functions, and/or the like for guiding users through motor fitness and function training.

Figure 9:
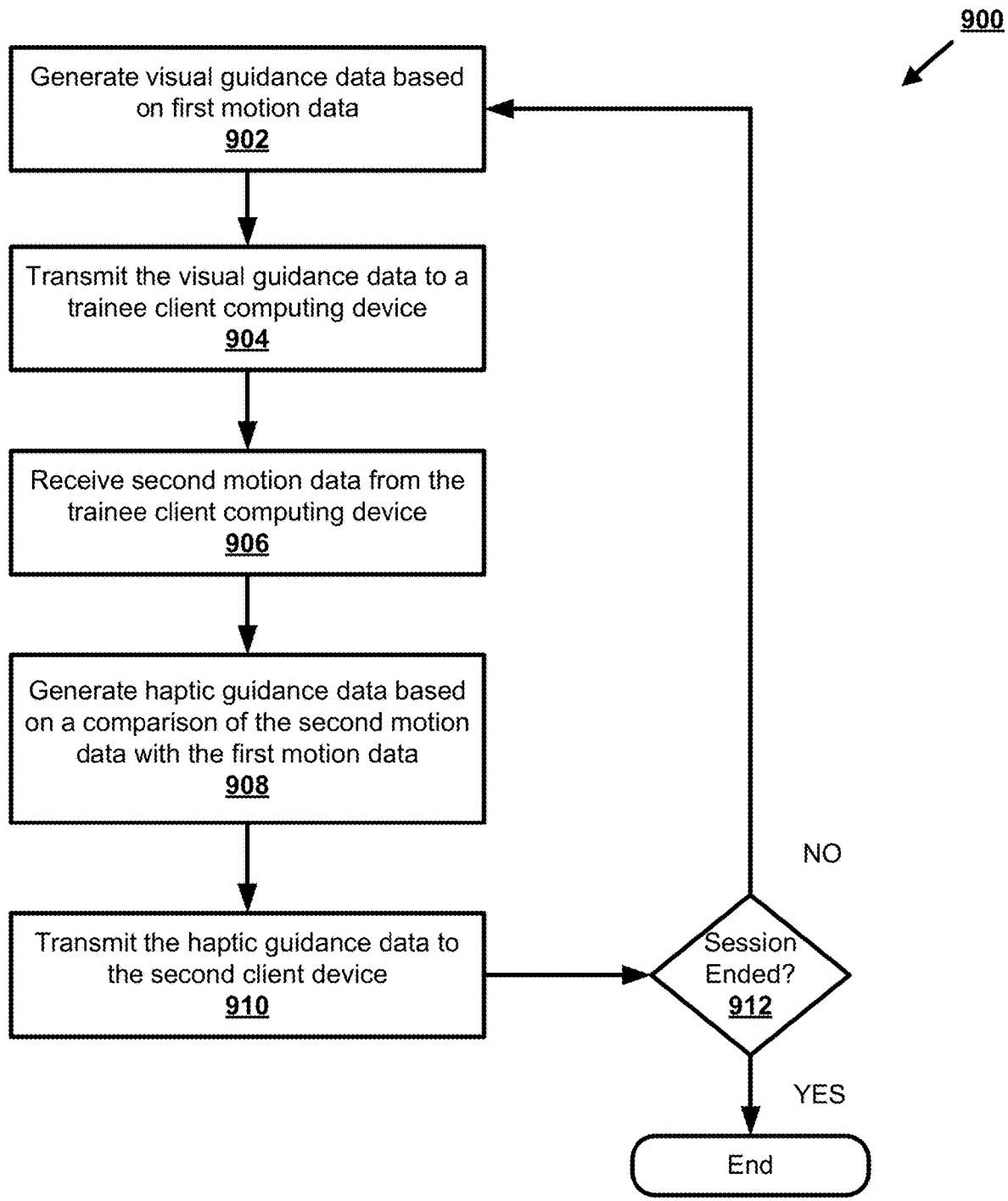
FIG. 9 depicts an example process for remote human motor training in accordance with some example embodiments described herein.

FIG. 9 depicts an example process for remote human motor training. The process 900 includes example operations that may be performed by the data processing server 105, and the data processing server 105 comprises means, such as processor component 301, memory element 303, communications interface 307, and/or the like, for performing the example operations.

In some embodiments, at step 902, the data processing server 105 generates visual guidance data based on first motion data. The first motion data may be received from a first client computing device. In some embodiments, the first motion data comprises data representative of movements captured of a trainer user of the first client computing device, for example, while performing a set of body training tasks, during a session. The first motion data may be generated by sensor devices, as disclosed herewith, coupled to the first client computing device. Generating the visual guidance data may comprise converting the first motion data into reconstructed animation renderings with a VR avatar, as disclosed in the description with respect to FIG. 5.

In some embodiments, at step 904, the data processing server 105 transmits the visual guidance data to a second client computing device. The visual guidance data may be rendered by the second client computing device as a virtual trainer comprising a VR avatar demonstrating the performance of sample motions for the trainee user to follow based on the first motion data. For example, the trainee user can observe motions of the virtual trainer from multiple view perspectives (e.g., the third-person view and the first-person view) and follow along. In some embodiments, a rendering of the visual guidance data may comprise a semi-transparent figure (e.g., representative of the trainee user associated with the first client computing device) for the trainee user associated with the second client computing device to align their body with.

In some embodiments, at step 906, the data processing server 105 receives second motion data from the second client computing device. The second motion data may comprise data representative of movements captured of a trainee user of the second client computing device. The second motion data may be generated by sensor devices, as disclosed herewith, coupled to the second client computing device. The second motion data can be used to track body movements, orientations, and muscle engagement of the trainee user.

In some embodiments, at step 908, the data processing server 105 generates haptic guidance data based on a comparison of the second motion data with the first motion data. The haptic guidance data may be based at least in part on a degree of discrepancy between the first motion data and the second motion data. In some embodiments, each of one or more body components of the trainee user may be analyzed for haptic feedback for each of one or more frames captured in motion data. The analysis may comprise identifying a body component associated with the trainee user, identifying a haptic receiver for the body component, determining a position of the body component on the trainee user based on the second motion data, determining a distance between the body component and any of one or more active haptic senders within k frames for a current frame, and activating the haptic receiver if the distance is less than a threshold value. Further details of the analysis are described in further detail above with respect to the description of FIG. 7.

In some embodiments, at step 910, the data processing server 105 transmits the haptic guidance data to the second client computing device. Transmitting the haptic guidance data may comprise triggering hapto-tactile feedback to a relevant body component. Hapto-tactile feedback may comprise vibration generated by haptic devices coupled to the second client computing device. The vibration may comprise an amplitude based at least in part on a degree of discrepancy between the first motion data and the second motion data (e.g., distance between a body component and any of one or more active haptic senders). In some embodiments, the hapto-tactile feedback comprises positive feedback representative of relatively accurate motion.

In some embodiments, at step 912, the data processing server 105 determines whether a current session has ended. If not, in some embodiments, the data processing server 105 continues to generate additional visual guidance data for the session and performs steps 902 through 910 until the session ends. Otherwise, in some embodiments, process 900 ends when the session ends.

Example Haptic System

Figure 10A:
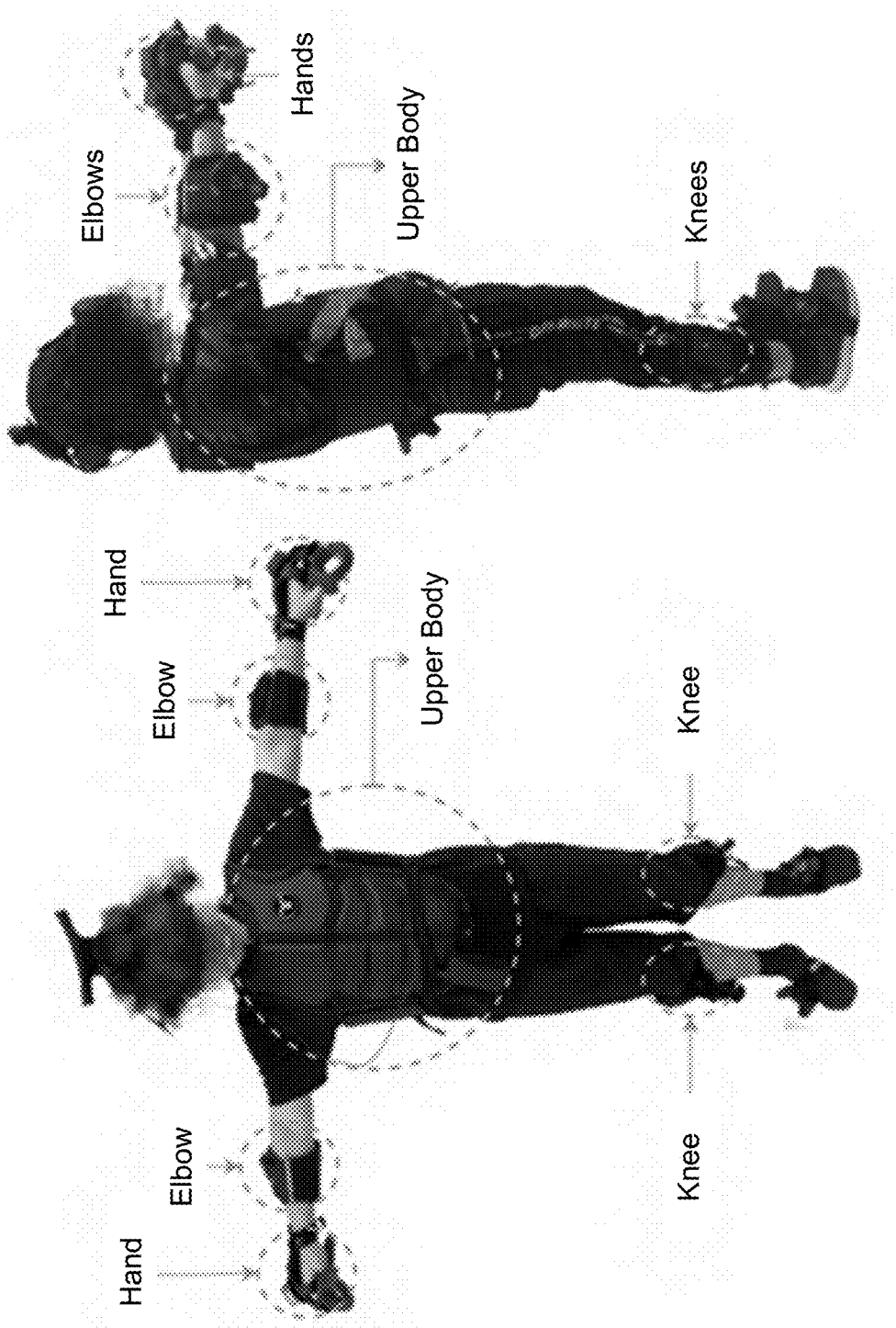
FIGS. 10A, 10B, and 10C illustrate exemplary deployment of a haptic simulation system in accordance with some example embodiments described herein.
Figure 10B:
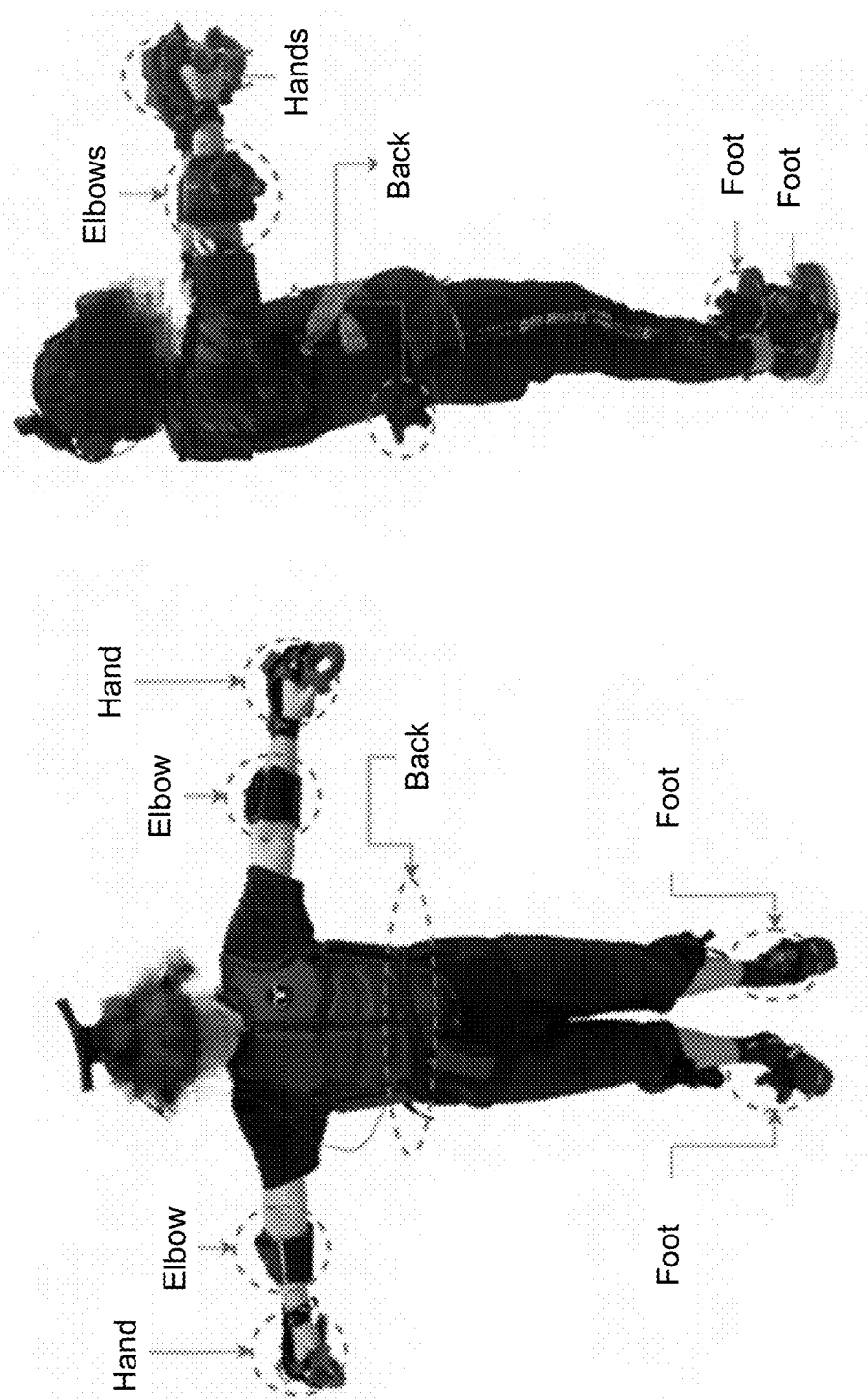
Figure 10C:
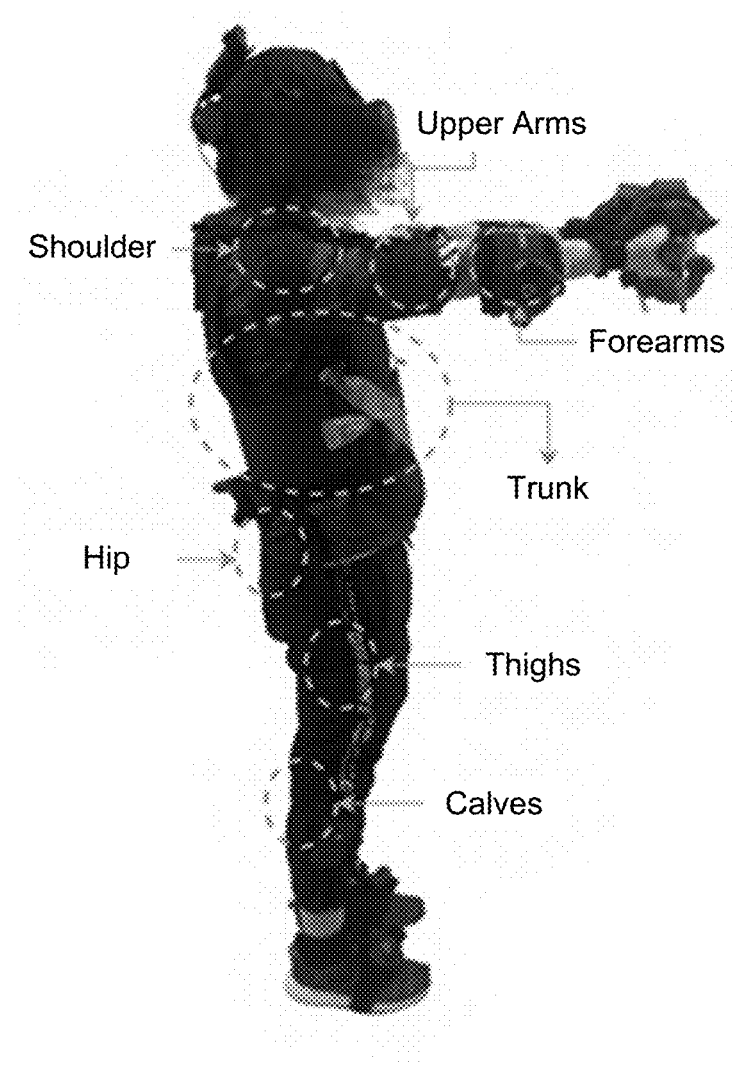

FIGS. 10A through 10C present example haptic and sensor configurations that may be worn by trainer and trainee users according to some embodiments of the present disclosure. Referring to FIG. 10A, a vest comprising a plurality of vibrotactile motors (e.g., 40) may be worn on the upper body. Haptic sleeves with motors (e.g., 12 each) may be placed at the left and right elbows. Two haptic gloves with motors (e.g., 6 each) may be placed at left and right hands, respectively. Motors may also be configured on knees. The selection of body locations for the vibrotactile motors may be based at least in part on the consideration of the key body parts involved in human motor activities or specific exercises. The vibration magnitude of haptic motors may be adjustable according to manufacturing guidance of the haptic devices (120 Hz at 3V input, with a strength of 5 g). As an example, the haptic motors may be configured to vibrate at an amplitude based at least in part on a degree of discrepancy between actual motion and target motion, such that the closer the motion to a target motion, the stronger the vibration experienced by the trainee (or vice versa).

Referring to FIG. 10B, sensors for detecting motion or physical activity may be placed on the lateral sides of the right and left elbows, on the back, and on the right and left feet. VR controllers and a headset may also track the hands and head, respectively. Data captured of a user by the sensors may be streamed, for example, into a game engine of the application server 406 to establish a connection between the user's physical motions in the real world and a virtual body or avatar in VR. Users may be able to see their body movement in VR which provides an immersive egocentric training scenario. In some embodiments, the game engine may calculate and broadcast data frame by frame instead of continuously.

Example Haptic Suit

In some embodiments, a haptic system may comprise a haptic suit that is capable of providing high fidelity haptic feedback and adapted to accommodate different exercise requirements. Haptic suits may comprise vests, sleeves, gloves, and pants. Each type of haptic suit may be designed to be flexible for haptic device placement. For example, a haptic suit may comprise a flexible and adjustable base structure constructed from lightweight and durable materials, such as high-strength fabric or polymer composites. The base structure may provide a comfortable fit for users of various body sizes and shapes. The base structure may cover a user's trunk and limbs. In some embodiments, an outer surface of the base structure comprises a hook-and-loop fastener (e.g., Velcro) which creates customized binding between the base structure and haptic devices.

The base structure of the haptic suit may be ergonomically designed to fit the natural contours of the human body. This may include features such as adjustable straps, stretchable panels, or padding located in strategic areas to ensure a secure fit and even distribution of pressure across a user's body. The haptic suit may also incorporate ventilation zones or mesh panels to improve airflow and reduce heat buildup during extended use. The base structure of the haptic suit may be equipped with standardized attachment points, such as screw threads, snap-fit connections, or magnetic attachment mechanisms. Such attachment points can be strategically placed on the front and back sides of the suit, allowing users to install, remove, or reposition the vibrating modules based on their specific needs.

FIG. 10C depicts an example layout of mounting bases for a haptic suit. The haptic suit depicted in FIG. 10C may comprise hook-and-loop fastener mounting bases at specific human motor control key points including upper arms, shoulder, forearms, trunk, hip, thighs, and calves. The mounting bases may be positioned to cover essential areas of the user's torso and limbs, allowing for precise and effective tactile feedback. The bases may be further designed as standardized attachment points, such as screw threads, snap-fit connections, or magnetic attachment mechanisms, to facilitate effortless installation and removal of vibrating modules. The placement of the mounting bases may also be based on human anatomy and kinesthetic perception, ensuring that vibrating modules can deliver tactile feedback effectively, regardless of their particular configuration. Such strategic placement may guarantee that vibrating modules are optimally positioned to provide a user with the most realistic and immersive experience possible.

Vibrating modules may be deployed in the disclosed haptic suit for generating whole-body or near whole-body coverage of haptic feedback to indicate complex motion features of an exercise or workout. A vibrating module may comprise a motor that generates vibrations felt by a user. The types of motors used for the vibrating module may comprise either a linear resonant actuator (LRA), or an eccentric rotating mass (ERM) motor.

A LRA motor may comprise a mass attached to a spring, driven by a voice coil actuator. When an alternating current (AC) is applied to an LRA motor, the mass may vibrate at its resonant frequency, resulting in highly precise and responsive vibrations. LRA are characterized by their low power consumption, fast response times, and wide frequency range, making them ideal for delivering high-fidelity tactile feedback.

An ERM motor may comprise a small, off-centered mass attached to a shaft of a DC motor. When the DC motor rotates, the imbalance caused by the off-center mass generates vibrations. ERM motors may be simpler in design, usually more affordable, and easier to integrate into a haptic suit. However, ERM motors may have slower response times and lower precision when compared to LRA motors.

However, by incorporating both LRA and ERM motors into vibrating modules of a haptic suit, users can experience a range of tactile feedback options. The LRA motors may provide high precision and responsiveness, while the ERM motors may offer a more affordable and easier-to-integrate option. The selection of motor type can be customized based on specific task requirements and user preferences.

A motor may be shielded by a housing to safeguard it against environmental factors such as dust, moisture, or impact. This housing may be typically crafted from lightweight materials like plastic or aluminum and may incorporate features such as ventilation to dissipate heat, noise reduction, or mounting points for attachment to the haptic suit.

A vibrating module may include a mounting interface that facilitates attachment or detachment from mounting bases on the haptic suit. The mounting interface may comprise screw threads, snap-fit connections, or a magnetic attachment mechanism, depending on specific requirements of a haptic suit's design. The mounting interface ensures a secure attachment of vibrating modules, while allowing users to tailor their haptic feedback by repositioning the vibrating modules.

In some embodiments, the haptic suit may further comprise a processing component. Vibrating modules may be connected to the processing component within a haptic suit. The processing component may be configured to receive motion evaluation and/or feedback data and translate it into corresponding vibration patterns. The processing component can be programmed based on different exercise and motion needs, providing versatility and adaptability. In some embodiments, the processing component may be configured to collect and send data, such as position, speed, and muscle activation features from IMUs and EMG sensors, to application server 406 and receive feedback data to generate vibration patterns for the vibrating modules. In addition, the processing component can adjust the vibration intensity, frequency, and duration based on the user's preferences or specific exercise motion requirements.

In some embodiments, the vibrating modules may be communicatively coupled to the processing component by electrical wiring, a flexible printed circuit (FPC), or through wireless protocols, such as Bluetooth or Wi-Fi. The connection enables the processing component to regulate the vibrating motor's functioning, such as controlling its vibration frequency, intensity, or duration based on hydrodynamic features. Furthermore, the connection can include data lines for monitoring the motor's performance, such as temperature or current consumption, which can aid in refining the haptic feedback and ensuring safe operation.

The performance of the vibrating modules may be optimized to improve the overall user experience by isolating the transmission of vibration from each vibrating module from the haptic suit's structure and other modules. This can be accomplished by integrating damping materials such as silicone or rubber into the vibrating module's design, which can absorb or dissipate vibrations. Additionally, isolation techniques like suspension systems or flexible mounts can be employed to prevent unwanted vibrations from affecting the user's experience. By minimizing unwanted transmission of vibrations, haptic feedback can be more precise and effective, enhancing user immersion and engagement.

In order to accommodate a variety of body sizes and shapes, the base structure of the haptic suit may provide a range of adjustability options, such as adjustable straps or belts, hook-and-loop closures, or elastic components that enable a secure and comfortable fit. The base structure of the haptic suit may also incorporate modular sizing, allowing users to add or remove sections of the base structure to customize the fit according to their body dimensions. By providing multiple adjustability options, the haptic suit can be adapted to fit a wide range of users, ensuring maximum comfort and effectiveness of haptic feedback. This flexibility also makes the haptic suit suitable for a variety of applications, as it can be adjusted to accommodate the specific needs of different tasks and environments.

To achieve optimal functionality and user experience, the base structure of the haptic suit may further comprise a design that seamlessly integrates its mechanical, electrical, and communication components. In some embodiments, the haptic suit may incorporate channels or compartments for routing wires, a processor component, or wireless communication modules. Proper integration of these components may ensure a clean and uncluttered design, minimizing the risk of damage to internal components and improving the durability and reliability of the haptic suit. By integrating these components effectively, the haptic suit can provide seamless tactile feedback to the user, enhancing their overall experience. This design approach also enables access and maintenance of the internal components, facilitating any necessary repairs or upgrades.

In some embodiments, the haptic suit is powered by a rechargeable battery pack which can also wire-connect to a power source. An efficient power management system may be implemented to maximize battery life and ensure safe operation, such as incorporating voltage regulators, current limiters, and thermal protection circuits.

Users may reconfigure the haptic suit's vibrator layout based on their specific needs or a recommended configuration map. For example, vibrating modules may be removed from less relevant body areas and installed in more relevant areas, optimizing tactile feedback experience. To streamline the reconfiguration process, the haptic suit can incorporate attachment mechanisms such as magnetic connections, snap-fit connectors, or twist-lock systems. Such attachment mechanisms may allow users to quickly and effortlessly move vibrating modules between different body areas.

In some embodiments, a customization software or smartphone/tablet application can provide step-by-step guidance on reconfiguring vibrating modules on the haptic suit based on their specific use case. A haptic suit user interface, either integrated directly into the haptic devices or accessible via a connected smartphone/tablet application executing on a client computing device in communication with the haptic suit, may enable users to monitor, configure, and adjust various settings related to haptic feedback, fit, and comfort. For example, users can use the user interface to adjust intensity, frequency, and duration of vibrations for each individual vibrating module, creating a personalized feedback profile that caters to their specific needs and preferences. The user interface may also provide options to adjust the haptic suit's fit and comfort, such as tightening or loosening straps, modifying padding, or altering the positioning of the vibrating modules.

Example Motion Performance Evaluation Methods

The trainer's and trainee's motions can be recorded in the same game engine environment with the same initial position. Trainees can be explicitly instructed to copy the behavior of the trainer to the greatest extent possible. For example, if provided a naturalistic scenario where people were asked to repeat a gym motion, different individuals will show variability in "how" they accomplish the motion (e.g., time and speed). But given that the purpose is to train the trainees with correct motion from the trainer, the performance measurement can focus on the motion trajectory alignment, e.g., how the motion trajectory of the trainee varies from the desired one. This may be the most relevant measure in the context of a motion task.

Human motor performance can be quantified by comparing the cumulative spatial offset across the seven selected body components between the trainer's motions and the trainee's motions, with the idea that the greater the error in cumulative joint position difference (discrepancy) between trainer's motion and the trainee's motion, the poorer the performance. Equation 2 may be used to evaluate trainee performance by measuring motion discrepancy:

$$g(i) = \sum_{n=1}^{m}(f(i,n)) \quad \text{Equation 2}$$

In the above equation, g(i) may represent the discrepancy for trial i, m may represent the number of selected body components (shown in FIG. 10B), $f(i, n)$ may represent the discrepancy between the trainee and trainer at trial i for component n. The criteria of selecting body location for analysis may be whether the selected gym motion engages such a body location.

Function $f(i, n)$ may be calculated in Pairwise Euclidean Distance (PED) and Interpolated Dynamic Time Wrapping (IDTW) to extract difference patterns. PED may be used for spatial similarity calculation. PED is indicated by the average Euclidean Distance between the trainee's position and trainer's position for each frame and each component as shown in the below equation:

$$f(i,n) = \frac{\sum_{k=1}^{t}(p_{i,n,k} - p'_{i,n,k})}{t} = \frac{\sum_{k=1}^{t}\sqrt{(dx_k^2 + dy_k^2 + dz_k^2)}}{t} \quad \text{Equation 3}$$

Figure 11A:
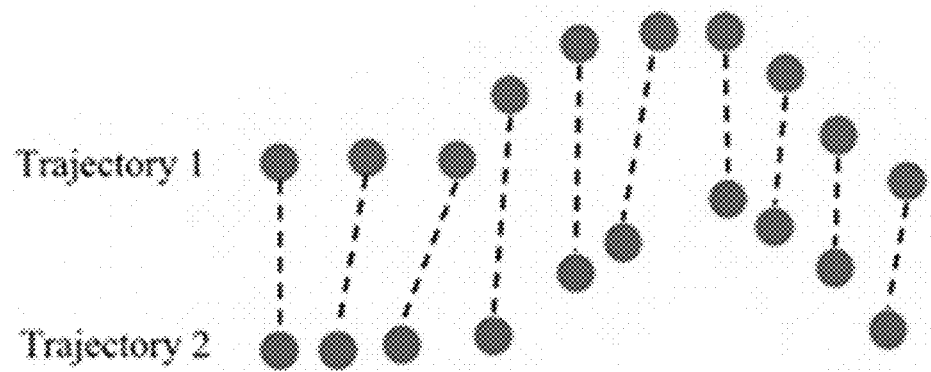
FIGS. 11A and 11B illustrate exemplary pairwise correlation between two trajectories in accordance with some example embodiments described herein.

In the above equation, i and n may represent the trial ID and component ID respectively, t may represent the number of effective frames; p and p' may represent the spatial arrays of the trainee and trainer respectively; $dx_k$, $dy_k$, $dz_k$ may represent the Euclidean distance between trainee and trainer at frame k in x, y, and z dimensions. PED takes the temporal correlation into account. In other words, a mismatch between velocities is considered in PED, which calculates the spatial-temporal discrepancy as shown in FIG. 11A.

Figure 11B:
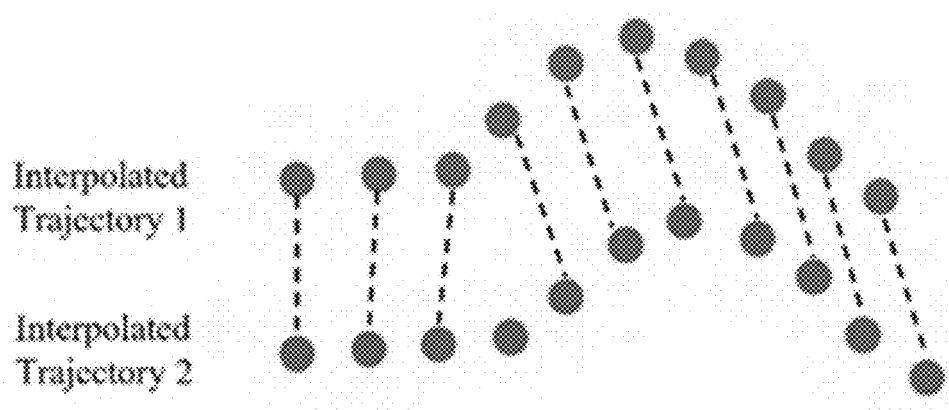

On the other hand, IDTW may emphasize the spatial discrepancy only. The datasets may be interpolated to smooth the curve such that the influence of velocity is decreased. Then IDTW method can be used to calculate the spatial discrepancy. IDTW may be used to compare the spatial similarity between two temporal sequences which may have different speeds. As shown in FIG. 11B, IDTW warps non-linearly in the time dimension to find the optimal shape match between two spatial trajectories. Comparing with PED, IDTW weakens the influence of time (speed) and thus provides results prone to a shape comparison. Both PED and IDTW may be applied to extract different features.

Example Experimental Implementation of Various Embodiments

The present application discloses a platform for transferring the motor skills of an expert trainer to a novice trainee. The motor task can include but is not limited to squats, push-ups, lifts, and yoga. Compared with traditional motion training method that uses 2D media (slides, documents, videos), the disclosed framework enables an egocentric training experiment as well as intuitive motion feedback loop (i.e., using haptic feedback to improve motion).

A human-subject experiment using 30 healthy participants was conducted to test the effectiveness of the proposed framework, as well as the marginal contributions of haptics-only against $3^{rd}$ person view motor training method. Since bending and lifting are common motions that result in musculoskeletal injuries in gym motion training, a standard power clean lift (PC) was chosen as the target motion for gym training. The PC starts with standing over the barbell and separating feet apart with hip width. Then the person needs to squat down and grip the bar, lift the barbell with shoulders over the bar and brace the trunk.

A gym trainer was recruited to perform PC motion wearing motion trackers. Trainees were instructed to perform the body workout tasks using a trainee module (e.g., trainee module 404). Recruited subjects were instructed to perform the PC task. View perspective as a variable was proved to be impactful for the learning process, and hence it was added as a control variable in this experiment. To validate the effectiveness of haptic sensation transfer, four conditions were designed with variances in view perspective and haptic feedback: third-person view (TPV), third-person view with haptic (TPVH), first-person view (FPV), and first-person view with haptic (FPVH). The controlled condition was TPV, in which novice trainees simply observed replayed motions in third-person view with no haptic cues. In the TPV condition, two virtual expert trainers performed correct motions in front of the subjects. One expert trainer was facing the participant while the other had their back facing the participant. Participants were asked to observe the two virtual expert trainers' motion whilst following the motion as accurately as possible, simulating a real-life scenario in which people learn how to perform the task through observing demonstrations from expert trainer. In the TPVH condition, haptic feedback was added, i.e., novice trainees could feel vibrations on their body parts with the haptic guidance system when the corresponding body components were moving accurately. In an egocentric visual condition, or "FPV," novice trainees could observe the motion from the first-person perspective.

The virtual avatar is semi-transparent so the novice trainees could see through the expert trainer while observing their motion. Trainees in FPV condition observed the semi-transparent virtual trainer performing target motions standing at the same location with the novice trainees. The novice trainees were instructed to align with the virtual expert trainer before starting and follow the motion accurately. The novice trainees observed the virtual expert trainer from an egocentric view, simulating the visual effect of doing the motion on their own. In addition to FPV, the FPVH condition activated positive haptic feedback when the novice trainee's motions were correct. In all conditions, novice trainees' tasks were to follow the expert trainer's motions as accurately as possible. This controlled experiment design could distinguish the effectiveness of haptic sensation transfer by comparing TPV with TPVH, and FPV with FPVH, while providing implications on the role of view perspectives. Novice trainees were asked to perform the task for six continuous trials per condition to examine performance improvements and learning.

Figure 12:
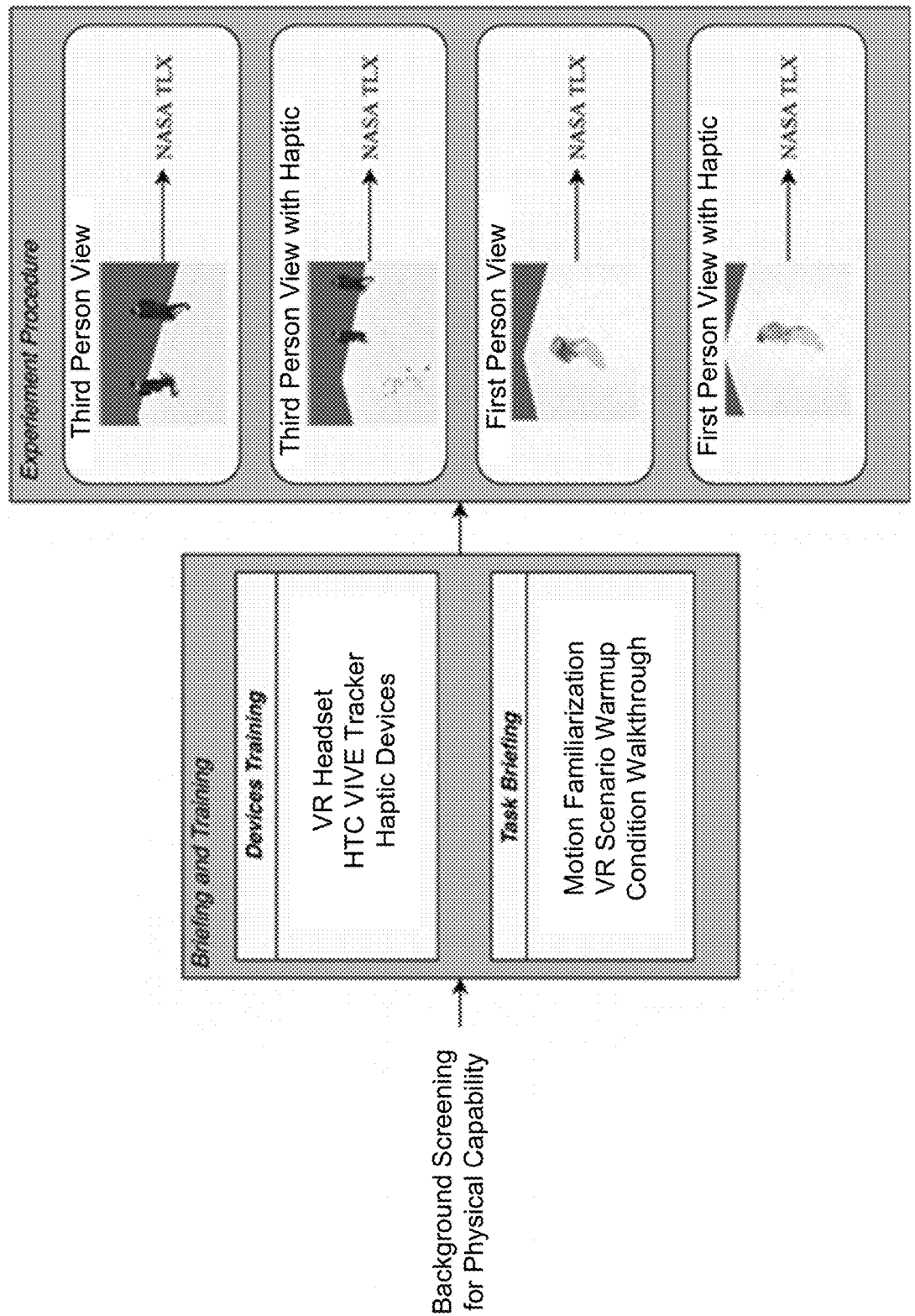
FIG. 12 illustrates an exemplary experiment procedure in accordance with some example embodiments described herein.

FIG. 12 depicts an experiment procedure. Human figures denote expert trainer's motion. Icons in space denote haptic senders and were invisible during the experiment. Thirty healthy participants, with no recent (last 12 months) musculoskeletal or neurological disorders were recruited in this study. Eligible participants were briefed on the experiment's purpose and procedure. The participants were facilitated to set up the VR headset, VIVE trackers, and the haptic devices. Then use of the devices was demonstrated to the participants. This experiment adopted a within-subject design to minimize individual differences. To rule out the initial adaptation process to the disclosed system from the final data, the experiment task (standard PC motion) was demonstrated in great detail and allowed participants to practice an example task with the system for three minutes.

After the pre-experiment briefing and training, the experiment WAS formally started. Each participant needed to go through all four conditions. The sequence of four conditions was randomly shuffled to further reduce the learning effect. A total of six trials were collected in each condition to reduce the significance of random error. A NASA TLX questionnaire was conducted after finishing all six trials in each condition. Participants were allowed to take a short break between each condition. Whole-body motion data was collected during the experiment, which was further processed in data analysis.

Figure 13A:
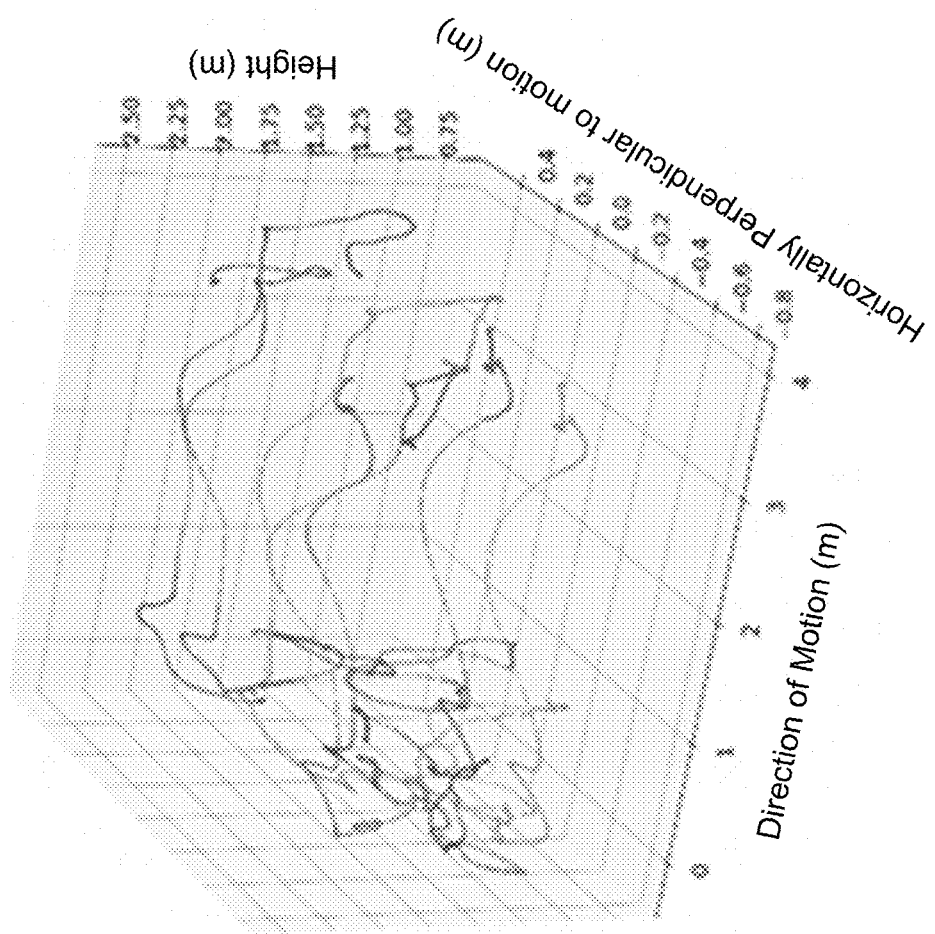
FIG. 13A and FIG. 13B illustrate motion trajectories of an exemplary experiment procedure in accordance with some example embodiments described herein.
Figure 13B:
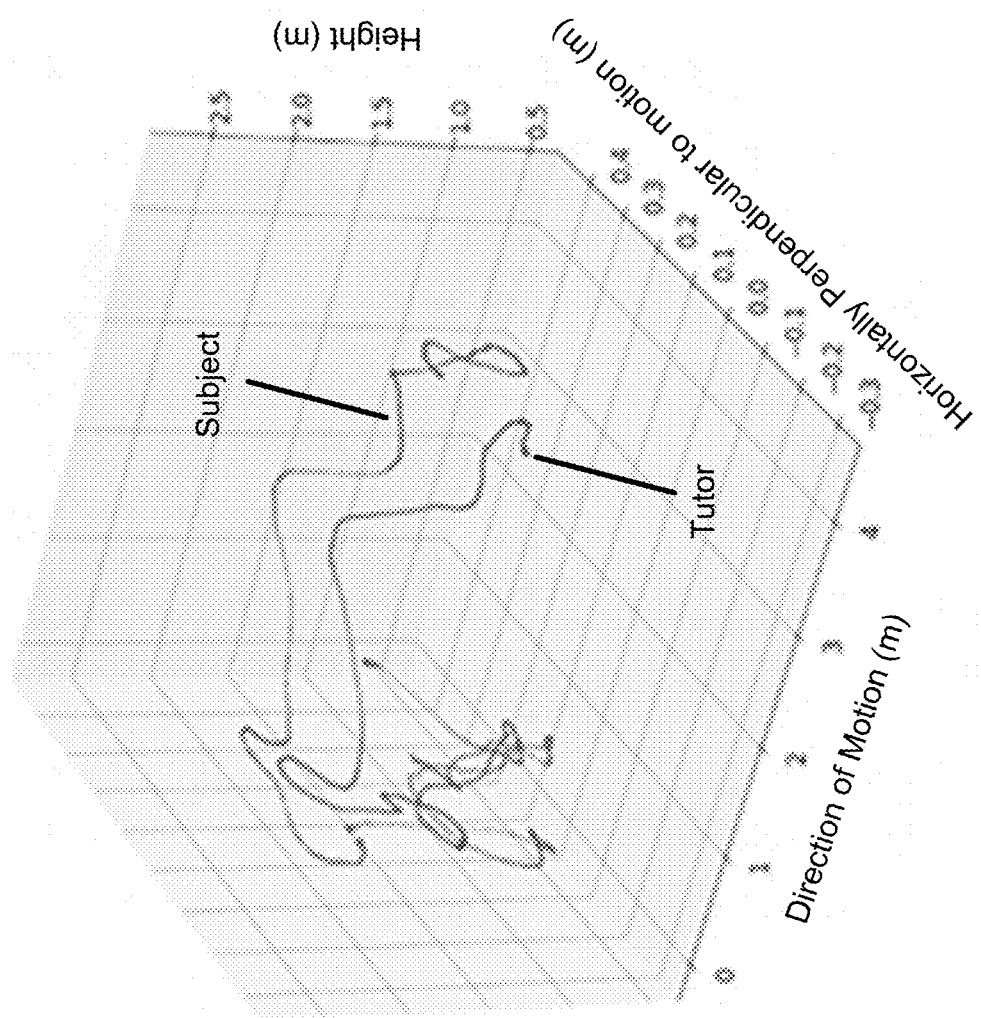

After reconstructing the virtual whole-body motion, the time series of the 3-dimensional spatial data of both hands, both elbows, waist, and both feet were sampled. The seven sampled positions were used to evaluate motion performance. FIGS. 13A and 13B depict visualizations of the trajectory of these sampled positions from a randomly selected trial. Each point in FIG. 13A represents the corresponding spatial position in one frame. FIG. 13A presents spatial position of selected body components including right and left hand, right and left elbow, waist, right and left foot. FIG. 13B presents a comparison of the trajectory between a trainee and the trainer's motion. Because the data were sampled with the same interval, the density of the data indicates the moving speed—with a faster movement leading to sparse data points. It shows that the data points were denser at some locations than others, suggesting that the participant's moving speed varied during the motion.

Six trials were collected in each condition for each participant. To reduce random error, two trials were grouped into one learning stage, i.e., early stage corresponded to trials one and two, middle stage corresponded to trials three and four, late stage corresponded to trials five and six. The task performance in each stage was evaluated by the average discrepancy of the corresponding two trials.

Learning rate (LR) may be one of the most important parameters evaluating learning effectiveness. In this 3-stage learning task, LR may be determined by dividing the late stage by the early stage. Considering that the stage performances are measured by the discrepancy, the inverse of the division may be calculated, where the LR θ is calculated by the following equation:

$$\theta = \left(\frac{D_3}{D_1}\right)^{-1} = \frac{D_1}{D_3} \qquad \text{Equation 4}$$

In the above equation, $D_1$ and $D_3$ may represent the discrepancy in early-stage and late-stage, respectively. If θ is larger than 1, it implies positive learning. The larger θ is, the higher LR is.

Example Experimental Results of Various Embodiments

The participants included 11 females and 19 males. Participants' age ranged from 19-32, with a median value of 25 years old. The participants on average did exercise 3.7 times per month with a median value of 4 times. 20 out of 30 participants had experienced VR previously. Table 1 summarized the demographic factors.

TABLE 1

Demographic Factors of Recruited Participants

| Demographic Factors | Response Range | Mean/ Percentage | Median |
|---|---|---|---|
| Gender | Male/Female | 63% Male | — |
| Age | 19-32 | 25.5 | 25 |

TABLE 1-continued

Demographic Factors of Recruited Participants

| Demographic Factors | Response Range | Mean/ Percentage | Median |
|---|---|---|---|
| Exercise Frequency (Per Month) | 0-12 | 3.7 | 4 |
| Existing VR Experience | Yes/No | 67% Yes | — |

Figure 14:
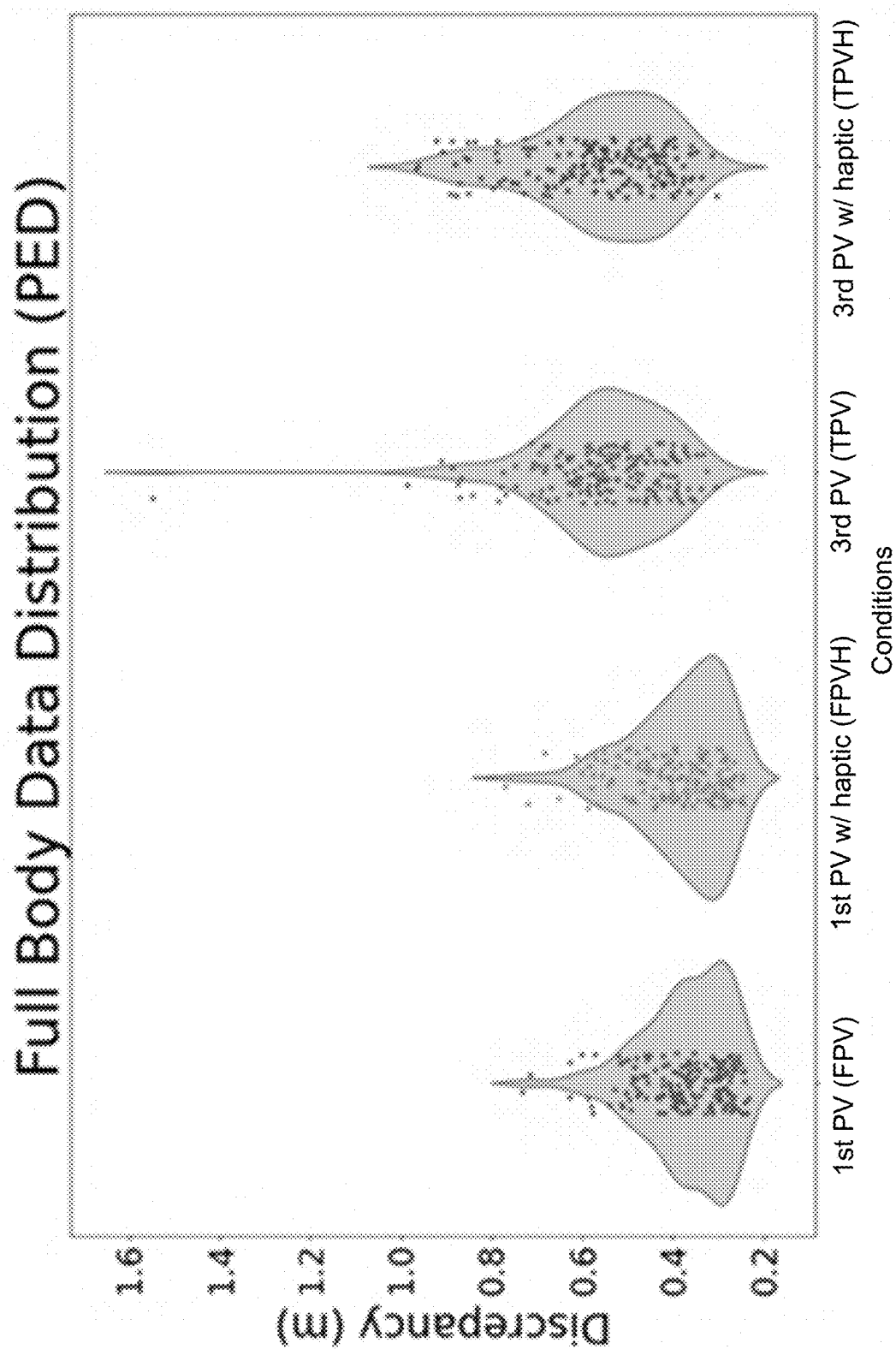
FIG. 14 illustrates whole-body overall discrepancy distribution of an exemplary experiment procedure in accordance with some example embodiments described herein.

FIG. 14 presents whole-body (all 7 tracked body components) discrepancy data across all trials, conditions, and participants. Each data point represents the average discrepancy in meters across 7 tracked positions for all frames in one trial. It was found that although the motion appeared simple and straightforward, it was difficult to follow the standard motion. The average spatial discrepancies varied from 5 to 35 cm, and sometimes higher. To minimize individual differences and form a comparison baseline, each subject's data was normalized by its standard deviation of discrepancies before the statistical test. In a normality test (Anderson Darling Test), the normality assumption was rejected (with confidence interval 95% for both analysis methods).

Figure 15:
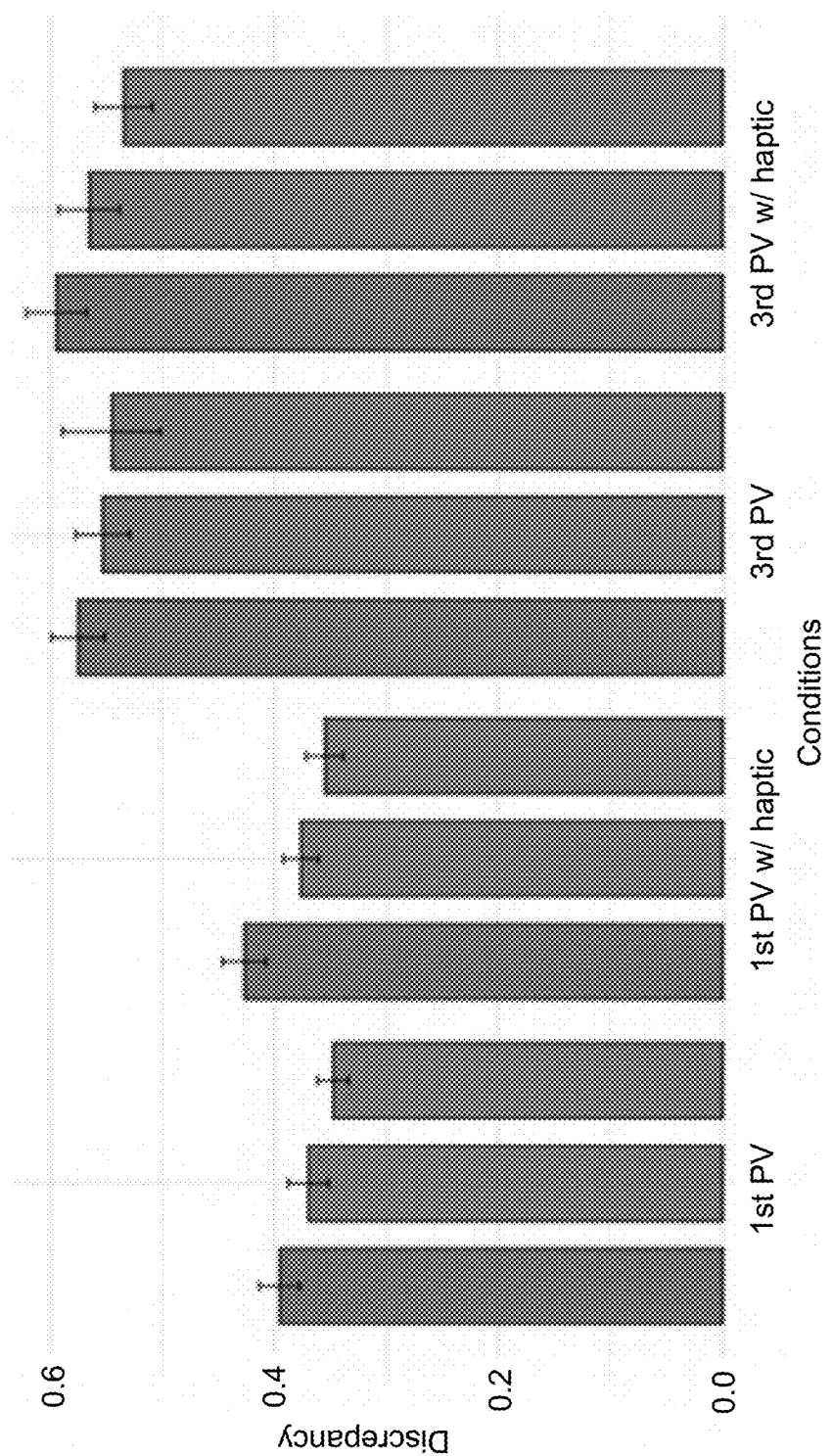
FIG. 15 illustrates exemplary task performance discrepancy in learning stages of an exemplary experiment procedure in accordance with some example embodiments described herein.

Non-parametric repeated measures (Friedman test) showed that there were significant differences between conditions ($p<0.001$), which implied that conditions did impose a significant impact on the task performance. The dataset was sub-divided into learning stages. FIG. 15 shows the task performance broken down into early, middle, and late stages.

A pairwise non-parametric post-hoc test (Wilcoxon signed-rank test) was conducted to estimate the effects of haptic feedback, and to estimate the effect of view perspective, separately. The Wilcoxon pairwise test was used to compare performances in the early stage, middle stage, and late stage of learning, as well as the Learning Rate (LR). Table 2 summarizes the Wilcoxon test results. PED results were generally non-significant except between the early stage of FPV and FPVH condition, with a p-value of 0.021; with FPVH condition producing worse results than FPV in the beginning. This indicates that in the first-person view, haptic feedback led to a deteriorated performance in the beginning and did not significantly influence performance in the later stages. This may be because the subjects were not used to the haptic feedback they received or due to some extra cognitive burden that subjects may have experienced.

Learning rate results were not significant between the conditions with or without haptic. PED results' learning rate had average and median values of 1.078 and 1.062 in condition TPV, 1.088 and 1.079 in condition TPVH, 1.109 and 1.111 in condition FPV, and 1.181 and 1.116 in condition FPVH. However, from the perspective of the average learning rate, the addition of haptic accelerated the motor learning process in general.

TABLE 2

Significance by Wilcoxon Test (whole-body performance)

| Comparison | p-value: TPV V.S. TPVH | p-value: FPV V.S. FPVH | p-value: TPV V.S. FPV | p-value: TPVH V.S. FPVH |
|---|---|---|---|---|
| All | 0.256 | 0.090 | <0.001* | <0.001* |
| Early Stage | 0.457 | 0.021* | <0.001* | <0.001* |
| Late Stage | 0.273 | 0.279 | <0.001* | <0.001* |
| LR | 0.877 | 0.192 | 0.517 | 0.039* |
| LR Mean (Median) | 1.078/1.088 (1.062/1.079) | 1.109/1.181 (1.111/1.116) | 1.078/1.109 (1.062/1.111) | 1.088/1.181 (1.079/1.116) |

The distribution patterns were also compared. Table 3 summarizes the distribution parameters of all conditions with different analysis methods. The result indicated that on average, the disclosed system reduced motion discrepancy by around 30% comparing with controlled condition (TPV).

TABLE 3

Overall Distribution Parameters

| Conditions | Expected Value | Median | Variance ($e^{-3}$) |
|---|---|---|---|
| TPV | 0.218 | 0.214 | 1.8 |
| TPVH | 0.223 | 0.222 | 1.8 |
| FPV | 0.148 | 0.144 | 1.5 |
| FPVH | 0.154 | 0.152 | 1.3 |

The experiment results indicated that the disclosed immersive haptic sensation transfer system impacted the motor learning process in a positive way. In general, the disclosed system improves gym motion learning by 30% on average, comparing with traditional learning method (watch video or observe the movement of the trainer). It was found that the disclosed system accelerated the PC lift motion learning process comparing to traditional learning methods.

To be specific, a human-subject experiment (n=30) was conducted to learn the PC Lift motion. The performance is evaluated with the summed average of spatial discrepancies between the participant's motions and the expert trainer's sample motions. The experiment result indicates that the first-person view motor training mode in the disclosed system, which visualizes motion information from an egocentric perspective, is significantly better than the traditional third-person view learning (such as watching videos or observing the motion of the trainer). The haptic feedback in the disclosed system increases the learning speed. The findings of this study suggests that first-person-view experience and haptic feedback may be an important feature to enhance human motor learning, especially in complex motor tasks or motions with high requirement on precision, such as gym training. In general, the proposed egocentric haptic sensation transfer method for gym training seems to be effective

CONCLUSION

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor but may be distributed in a modular fashion among a number of different computers or processors to implement various aspects of the present disclosure.

The terms "substantive," "substantial," and "substantially" may be used herein to relate to around 5%, 10%, 20%, 50% and/or 80% in different embodiments.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based at least in part on any suitable technology and may operate according to any suitable protocol and may include wireless networks, wired networks, or fiber optic networks.

The acts performed as part of the methods may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The invention claimed is:

1. A computerized method for remote human motor training, the method comprising:
   generating, by one or more processors, visual guidance data based on first motion data originating from a first client computing device;
   transmitting, by the one or more processors, the visual guidance data to a second client computing device;
   receiving, by the one or more processors, second motion data originating from the second client computing device;
   identifying, by the one or more processors, a hapto-tactile point on a haptic device based on a first frame of the first motion data, wherein (a) the haptic device is associated with the second client computing device, (b) the hapto-tactile point is associated with a second frame from the second motion data that respectively corresponds to the first frame from the first motion data, (c) the hapto-tactile point is configured at a second body component that is associated with the second motion data, and (d) the second body component corresponds to a first body component that is associated with the first motion data;
   generating, by the one or more processors, haptic guidance data that is associated with the hapto-tactile point based on a spatial-temporal difference between the second motion data with the first motion data; and
   transmitting, by the one or more processors, the haptic guidance data to the second client computing device.

2. The computerized method of claim 1, wherein transmitting the haptic guidance data further comprises triggering hapto-tactile feedback.

3. The computerized method of claim 2, wherein the hapto-tactile feedback comprises vibration based on a degree of discrepancy between the first motion data and the second motion data.

4. The computerized method of claim 1, wherein the haptic guidance data comprises positive feedback representative of relatively accurate motion with respect to an exercise or activity based on the spatial-temporal difference.

5. The computerized method of claim 1, wherein the haptic guidance data comprises feedback on one or more of body positioning, muscle activation, or movement pacing and control.

6. The computerized method of claim 1 wherein the first motion data comprises data representative of motion of a first user performing a set of body training tasks.

7. The computerized method of claim 1 further comprising:
   formatting the first motion data into a filmbox format;
   registering one or more animation components to the formatted first motion data; and
   configuring animation of the one or more animation components by linking the formatted first motion data to motion of a virtual reality avatar.

8. The computerized method of claim 7, wherein registering the one or more animation components further comprises mapping motion tracking points based on the first motion data to the virtual reality avatar.

9. The computerized method of claim 7 further comprising:
   accessing animation files associated with the formatted first motion data; and
   attaching the animation files to animation controllers configured to control motion of the virtual reality avatar.

10. The computerized method of claim 1 further comprising:
    identifying one or more haptic senders;
    identifying a haptic receiver of a plurality of haptic receivers for the second body component;
    determining a distance between the second body component and a haptic sender of the one or more haptic senders that is associated with the second body component is less than a threshold value; and
    triggering the haptic receiver based on the distance.

11. The computerized method of claim 10, wherein determining the distance between the second body component and the haptic sender further comprises determining positional data of the second body component for a trainee user based on the second motion data.

12. The computerized method of claim 10 further comprising comparing positional data of at least the second body component with positional data of the one or more haptic senders.

13. The computerized method of claim 1, wherein the visual guidance data comprises a virtual trainer demonstrating performance of sample motions for a second user associated with the second client computing device to follow.

14. The computerized method of claim 1 wherein the visual guidance data comprises a semi-transparent figure for a second user associated with the second client computing device to align bodies with a first user associated with the first client computing device.

15. A system for remote human motor training, the system comprising:
an application server configured to:
generate visual guidance data based on first motion data originating from a trainer module;
transmit the visual guidance data to a trainee module;
receive second motion data originating from the trainee module;
identify a hapto-tactile point on a haptic device based on a first frame of the first motion data, wherein (a) the haptic device is associated with the trainee module, (b) the hapto-tactile point is associated with a second frame from the second motion data that respectively corresponds to the first frame from the first motion data, (c) the hapto-tactile point is configured at a second body component that is associated with the second motion data, and (d) the second body component corresponds to a first body component that is associated with the first motion data;
generate haptic guidance data that is associated with the hapto-tactile point based on a spatial-temporal difference the second motion data with the first motion data; and
transmit the haptic guidance data to the trainee module.

16. The system of claim 15, wherein the first motion data comprises data representative of motion of a first user performing a set of body training tasks.

17. The system of claim 15, wherein the haptic guidance data comprises positive feedback representative of relatively accurate motion with respect to an exercise or activity based on the spatial-temporal difference.

18. The system of claim 15, wherein the haptic guidance data comprises feedback on one or more of body positioning, muscle activation, or movement pacing and control.

19. The system of claim 15, wherein the application server is further configured to:
identify one or more haptic senders;
identify a haptic receiver of a plurality of haptic receivers for the second body component;
determine a distance between the second body component and a haptic sender of the one or more haptic senders that is associated with the second body component is less than a threshold value; and
trigger the haptic receiver based on the distance.

20. One or more non-transitory computer-readable storage media including instructions that, when executed by one or more processors, cause the one or more processors to:
generate visual guidance data based on first motion data originating from a first client computing device;
transmit the visual guidance data to a second client computing device;
receive second motion data originating from the second client computing device;
identify a hapto-tactile point on a haptic device based on a first frame of the first motion data, wherein (a) the haptic device is associated with the second client computing device, (b) the hapto-tactile point is associated with a second frame from the second motion data that respectively corresponds to the first frame from the first motion data, (c) the hapto-tactile point is configured at a second body component that is associated with the second motion data, and (d) the second body component corresponds to a first body component that is associated with the first motion data;
generate haptic guidance data that is associated with the hapto-tactile point based on a spatial-temporal difference the second motion data with the first motion data; and
transmit the haptic guidance data to the second client computing device.

* * * * *